United States Patent [19]

Atanasoska

[11] Patent Number: 5,788,666
[45] Date of Patent: Aug. 4, 1998

[54] IONTOPHORESIS ELECTRODE

[75] Inventor: Ljiljana Atanasoska, Edina, Minn.

[73] Assignee: Empi, Inc., St. Paul, Minn.

[21] Appl. No.: 490,686

[22] Filed: Jun. 15, 1995

[51] Int. Cl.[6] ............................................. A61N 1/30
[52] U.S. Cl. ............................................................ 604/20
[58] Field of Search ............................ 604/20, 289, 304;
607/115; 128/639

[56] References Cited

U.S. PATENT DOCUMENTS

| | | | |
|---|---|---|---|
| 4,126,126 | 11/1978 | Bare et al. | 128/639 |
| 4,362,165 | 12/1982 | Carmon et al. | 128/640 |
| 4,374,204 | 2/1983 | Alexandrov et al. | 521/28 |
| 4,383,529 | 5/1983 | Webster | 604/20 |
| 4,416,274 | 11/1983 | Jacobsen et al. | 604/20 |
| 4,474,570 | 10/1984 | Ariura et al. | 604/20 |
| 4,702,732 | 10/1987 | Powers et al. | 604/20 |
| 4,719,241 | 1/1988 | Yates | 521/28 |
| 4,722,726 | 2/1988 | Sanderson et al. | 604/20 |
| 4,731,049 | 3/1988 | Parsi | 604/20 |
| 4,731,926 | 3/1988 | Sibalis | 29/877 |
| 4,744,787 | 5/1988 | Phipps et al. | 604/20 |
| 4,747,819 | 5/1988 | Phipps et al. | 604/20 |
| 4,752,285 | 6/1988 | Petelenz et al. | 604/20 |
| 4,786,277 | 11/1988 | Powers et al. | 604/20 |
| 4,820,263 | 4/1989 | Spevak et al. | 604/20 |
| 4,886,489 | 12/1989 | Jacobsen et al. | 604/20 |
| 4,915,685 | 4/1990 | Petelenz et al. | 604/20 |
| 4,921,475 | 5/1990 | Sibalis | 604/20 |
| 4,927,408 | 5/1990 | Haak et al. | 604/20 |
| 4,973,303 | 11/1990 | Johnson et al. | 604/20 |
| 5,084,006 | 1/1992 | Lew et al. | 604/20 |
| 5,087,241 | 2/1992 | Mathiesen et al. | 604/20 |
| 5,087,242 | 2/1992 | Petelenz et al. | 604/20 |
| 5,125,894 | 6/1992 | Phipps et al. | 604/20 |
| 5,135,477 | 8/1992 | Untereker et al. | 604/20 |
| 5,158,537 | 10/1992 | Haak et al. | 604/20 |
| 5,302,172 | 4/1994 | Sage, Jr. et al. | 604/20 |
| 5,328,455 | 7/1994 | Lloyd et al. | 604/20 |
| 5,362,308 | 11/1994 | Chien et al. | 604/20 |
| 5,423,739 | 6/1995 | Phipps et al. | 604/20 |
| 5,558,632 | 9/1996 | Lloyd et al. | 604/20 |

FOREIGN PATENT DOCUMENTS

| | | |
|---|---|---|
| 629790 | 8/1992 | Australia . |
| 2184016 | 6/1987 | United Kingdom . |
| PCT/US94/ 10960 | 4/1995 | WIPO . |

OTHER PUBLICATIONS

"The Synthesis of Ion Exchange Resins," *Ion Exchange Membranes* 1958, Wiley (New York) pp. 73–105.

March, J.; Advanced Organic Chemistry 263–269 (New York 1992).

Braun, T., et al.; Ion–exchange Foam Chromatography — Part I. Preparation of Rigid and Flexible ion–Exchange Foams; Analytica Chimical Acta.; pp. 45–54, vol. 64 (Amsterdam 1973).

Dobbin, P.S., et al.; Study of Hydrogen Bonding in 1–Ethyl–2–methyl–4–oxo–1, 4–dihydro–pyridin–3–yloxyethanoic acid and 3–(1, 2–Diethyl–4–oxo–1,4–dihydro–pyridin–3–yloxy)propanoic Acid by $^1$H NMR Spectroscopy and X–Ray Crystallography; J. Chem. Soc. Perkin Trans.; vol. 2, pp. 451–455 (1993).

Maresca, L., et al.; On the Carbon Nucleophilicity of Proton Sponge; J. Chem. Soc. Dalton Trans.; pp. 1867–1868 (1992).

(List continued on next page.)

*Primary Examiner*—Mark Bockelman
*Assistant Examiner*—Ellen Tao
*Attorney, Agent, or Firm*—Kinney & Lange, P.A.

[57] ABSTRACT

An iontophoresis electrode that includes a reservoir for holding electrolytic solution, a pH buffer, the pH buffer immobilized within the reservoir and the pH buffer having a buffering capacity of at least about 0.5 milliequivalents of acid or base per gram of pH buffer, and an electrical connection in electrical communication with the reservoir.

15 Claims, 1 Drawing Sheet

OTHER PUBLICATIONS

Bardez, E., et al.; Behaviour of "Proton Sponge" in Water-containing Reverse Micelles; Chemical Physics Letters; vol. 141, No. 3, pp. 261–266 (Nov. 6, 1987).

Bencini, A., et al., Synthesis and Characterization of an Aza–cage Behaving as a Proton Sponge — Crystal Structures of its Mono–and Tri–protonated Species; J. Chem. Soc. Perkin Trans.; vol. 2, pp. 115–120 (1993).

Bianchi, A., et al.; The Small Cage 12,17–Dimethyl–5–oxa–1,9,12,17–tetra–azabicyclo[7.5.5] nonadecane (L): its Synthesis, Characterization and 'Proton Sponge' Bhaviour. The Crystal Structure of the Dipicrate Salt [$H_2$(L)](Picrate)$_2$; J. Chem. Soc. Perkin Trans.; vol. II, pp. 1131–1137 (1989).

Bridger, N. J., et al.; Electrochemical Ion Exchange; J. Chem. Tech. Biotechnol.; vol. 50, pp. 469–481 (1991).

IONTOPHORESIS ELECTRODE

BACKGROUND OF THE INVENTION

The present invention generally relates to an apparatus and a method for transdermally delivering medicament ions derived from ionic substances, such as drugs or other therapeutic chemicals. More particularly, the present invention relates to an apparatus and a method of iontophoretically introducing medicament ions into a body.

Iontophoresis may be generally described as a method of transdermally introducing medicament ions into a body. The iontophoresis process utilizes current developed by an electric field to drive medicament ions through the skin, or other surface, and into the body. The iontophoresis process has been found to be particularly useful in transdermal administration of medicament ions, such as charged organic medications and therapeutic metal ions.

Iontophoresis permits introduction of medicament ions directly into a patient's tissues and blood stream without the need for a needle-based injection, which typically causes pain and may create a risk of infection. Iontophoretic delivery of medicament ions also avoids premature metabolism of medicament ions that typically occurs when drugs are taken orally. Premature metabolism is of concern because medicament ions derived from drugs that are taken orally are absorbed into the blood stream from the digestive system. The blood containing the medicament ions then percolates through the liver, where the medicament ions may be prematurely metabolized, before the medicament ions arrive at the target tissue. Thus, a substantial amount of the medicament ions derived from an orally administered drug may be metabolically inactivated before the medicament ions have a chance to pharmacologically act in the body.

A typical iontophoresis device includes two electrodes. One of the electrodes is often characterized as an "active" electrode and the other electrode is often characterized as a "ground" electrode. Also, one of the electrodes is a positively charged anode and the other electrode is a negatively charged cathode. Both electrodes are in intimate electrical contact with the skin or other surface of the body, which may be a human body or another type of body, such as an animal body. Application of electric current to the active electrode drives the medicament ion, such as the charged organic medication, from the active electrode into the body. The other electrode, the ground electrode, closes the electrical circuit and permits current flow through the active electrode and through the body.

In some cases, medicament ions may be delivered to the body from both electrodes of the iontophoresis system. In such cases, a first electrode is the active electrode for a first medicament ion that is delivered from the first electrode, and a second electrode is the ground electrode with respect to the first medicament ion. Similarly, the second electrode is the active electrode for a second medicament ion that is delivered from the second electrode and the first electrode is the ground electrode with respect to the second medicament ion. Typically, the first and second medicament ions are different in polarity and in chemical structure from each other.

A variety of patents discuss iontophoresis systems, iontophoresis electrodes, and/or methods of iontophoretically administering medicament ions. Examples of these patents include U.S. Pat. Nos. 4,744,787 to Phipps et al.; 4,752,285 to Petelenz et al.; 4,820,263 to Spevak et al.; 4,886,489 to Jacobsen et al.; 4,973,303 to Johnson et al.; and 5,125,894 to Phipps et al.

Some patents provide details about the reservoirs of electrodes. For example, U.S. Pat. No. 4,702,732 to Powers et al. describes the reservoir in terms of a polymer matrix. The Powers patent comments that, when the polymeric matrix is hydroxyethyl methacrylate, a hydrogel, the pharmacologically active ligand may be added to the hydrogel reaction mixture prior to polymerization or may be introduced into the hydrogel matrix after formation of the matrix. U.S. Pat. No. 5,302,172 to Sage, Jr. et al. comments that the reservoir containing the active agent to be delivered may be made of a variety of materials, including foams, ion-exchange resins, gels, matrices. Also, U.S. Pat. No. 5,328,455 to Lloyd et al. describes a multi-layer hydrogel reservoir of an iontophoretic electrode that may incorporate ion-exchange resin Other references describe incorporation of ion-exchange substances into devices other than buffered electrodes. For example, Braun, *Analtlica Based Chimica Acta*, Vol. 64, pp. 45–54 (1973), comments upon preparation of ion-exchange foams for use in ion-exchange foam chromatography. The Braun reference mentions preparation of homogeneous ion-exchange foams by introduction of ion-exchange groups onto a previously prepared plastic foam, such as by surface or penetrating treatment. The Braun reference also discusses preparation of heterogeneous ion-exchange foams by foaming a cation exchange material, in powder form, with precursors of an open cell polyurethane foam. Also, Australian Pat. No. 629,790 describes an electrode that is used in wastewater treatment and water desalinization processes for recovering metals. The electrode incorporates a polyurethane foam that includes ion-exchange resin.

Though iontophoresis system technology has realized several advances, numerous problems remain to be solved and many opportunities for enhancing performance remain. Examples of some suggested changes for further optimizing iontophoresis systems are included in U.S. Pat. Nos. 4,731,049 to Parsi; 4,915,685 to Petelenz et al.; and 5,302,172 to Sage, Jr. et al. For example, the Parsi patent suggests a change in the iontophoresis system that is said to increase the types of drugs deliverable by iontophoresis systems. Also, the Petelenz patent suggests changes that are said to enhance the proportional relationship between the amount of medicament administered and current flow. Finally, the Sage, Jr. patent discloses the use of vasodilators in iontophoresis as a means of enhancing delivery of an active agent that is delivered along with the vasodilator.

Despite the many advances in iontophoresis technology, a series of problems remain that relate to electrolysis of water in iontophoresis system electrodes. As an example, current passing through the electrodes of an iontophoresis system typically causes electrolysis of water. In the anode, the electrolysis reaction proceeds as follows:

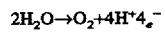

In the cathode, the electrolysis reaction proceeds as follows:

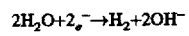

Since an operational iontophoresis system includes both an anode and a cathode, both hydrogen ions ($H^+$) and hydroxide ions ($OH^-$) are produced during system operation. Absent buffering, the hydrogen ion concentration will increase at the anode and the hydroxide ion concentration will increase at the cathode.

The hydrogen ion and hydroxide ion accumulation in the electrodes of iontophoresis systems is problematic for a variety of reasons. For example, the increased hydrogen ion concentration shifts the pH downward at the anode, and the increased hydroxide ion concentration shifts the pH upward at the cathode. The pH shift typically causes at least minor skin irritation and can cause severe burning of a patient's skin. Also, the pH shift can change the activity of the medicament ion(s) being delivered by the electrode and can even degrade the physical properties of the electrode components.

A variety of changes in the operation and structure of iontophoresis systems have been suggested to control or minimize the pH shift caused by electrolysis of water. For example, U.S. Pat. No. 4,886,489 to Jacobsen et al. discloses a flow-through electrode in which hydrogen ions or hydroxide ions produced during iontophoresis are constantly removed. As a result of the flushing, the Jacobsen patent alleges that the pH within the iontophoresis system can be maintained within desired levels without addition of buffers. However, though the Jacobsen flushing system may help to maintain desirable pH levels, addition of the flushing mechanism unnecessarily complicates the iontophoresis system. Also, the flushing mechanism removes desirable, and sometimes expensive, medicament ions. Additionally, the flushing mechanism is a dynamic solution as opposed to a more desirable static solution to the pH shift problem, such as an improved buffering system.

The Petelenz patent, U.S. Pat. No. 4,752,285, discloses an iontophoresis system that includes a reactive electrode and control of voltage in the system. The Petelenz '285 patent mentions a silver electrode and a lead electrode as examples of the reactive electrode. According to the Petelenz '285 patent, use of the reactive electrode permits iontophoresis to occur, at select medicament and complimentary ion concentrations and at select voltage, without electrolysis of water and consequent pH shift. However, the present inventor has found that these comments of the Petelenz '285 patent about the absence of water electrolysis and pH shift are inaccurate.

Specifically, the present inventor has determined that metal oxides typically form on the reactive metal electrode prior to use of the reactive metal electrode in accordance with the Petelenz '285 patent. The metal oxides of the reactive metal electrode, such as silver oxide that forms on the reactive silver electrode, support electrolysis of water in the iontophoresis system. The electrolysis of water that occurs creates localized pH shifts of sufficient magnitude to cause localized irritation of patient's skin during iontophoretic use of the Petelenz '285 electrode. Another concern is that the Petelenz '285 system is said to control the pH shift without addition of buffering ions. However, this solution to the pH shift problem introduces a precipitate. Though the precipitate is said to be practically insoluble in the transport medium, any precipitate that does solubilize will compete with the medicament ion for delivery to the body.

Another technique for controlling the pH shift involves introduction of one or more buffering species into the iontophoretic electrodes. The buffering species may be in solution with the medicament ion to be delivered. However, when the buffering species is in solution with the medicament ion, experience has shown that the buffer species and derivatives of the buffer species remain mobile within the electrode and undesirably compete with medicament ions for delivery to the body. Alternatively, the buffering species may be immobilized within the iontophoresis electrode, as disclosed in U.S. Pat. No. 4,973,303 to Johnson et al. The buffered electrode disclosed in the Johnson patent significantly reduces the problem associated with mobile buffering species. However, it has been found that the amount of ion-exchange functionality included in the buffer of the Johnson buffered electrode can not be accurately controlled.

Though many advances in iontophoretic electrode design and operation have been realized, challenges requiring solution remain. For example, less complicated and more accurate techniques are needed for controlling the amount of ion-exchange functionality included on immobilized buffers. Also, opportunities remain for simplifying the structure and the manufacture of iontophoresis electrodes. Finally, opportunities remain for further reducing competing ion concentrations in iontophoresis systems.

SUMMARY OF THE INVENTION

The present invention includes a pH buffered electrode with a reservoir for holding electrolytic solution, a pH buffer that is immobilized within the reservoir and an electrical connection in electrical communication with the reservoir. The pH buffer has a buffering capacity of at least about 0.5 milliequivalents of acid or base per gram of pH buffer. The present invention further includes an iontophoresis electrode, a method of making an iontophoresis electrode, and a method of making a pH buffered electrode.

DETAILED DESCRIPTION OF THE PREFERRED EMBODIMENTS

Figure 1:
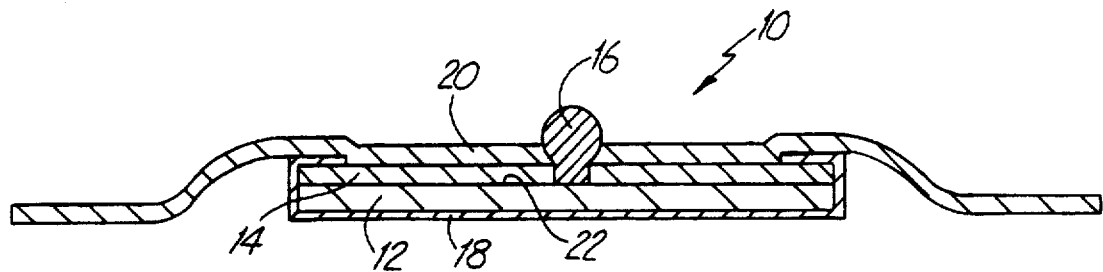
FIG. 1 is a sectional view of a pH buffered electrode of the present invention.

An iontophoresis electrode of the present invention is generally depicted at 10 in FIG. 1. The electrode 10 includes a reservoir 12 that contains an electrolytic solution of medicament ions and complimentary ions of the medicament ions. The electrode 10 also includes a conductive layer 14 that is located adjacent to the reservoir 12. The electrode 10 further includes a conductive terminal 16 that is attached to the conductive layer 14. The terminal 16 couples the electrode 10 to a source of electrical power (not shown), such as a source of direct current. The electrode 10 also includes a wicking wrap 18 that holds the reservoir 12 and the conductive layer 14 together. An adhesive covering 20 may also be attached to the conductive layer 14 opposite the reservoir 12 to aid in adhering the electrode 10 to a surface (not shown), such as the skin of a human or animal body.

Any substance that is to be iontophoretically delivered to the body exists as medicament ions. The electrolytic solution that is included in the electrode 10 may include one or more different types of medicament ions. Charged organic medications and therapeutic metal ions are examples of medicament ions. It will be appreciated that transportation of medicament ions through the skin of the human or animal body takes place in an electrical field such as that produced in an iontophoresis system that includes two electrodes, as well as, a source of electrical current.

The medicament ions that are present in the electrolytic solution may be derived from any suitable ionic substance. The ionic substance may be any suitable salt, acid, or base that dissociates into medicament ions, and complimentary ions of the medicament ions, in the electrolytic solution. Medications, drugs, and other therapeutic chemicals are some general examples of suitable ionic substances. Some examples of particular ionic substances that may evolve medicament ions in the electrolytic solution include morphine sulfate, dexamethasone sodium phosphate, hydrocortisone derivatives, magnesium chloride, lidocaine hydrochloride, morphine hydrochloride, steroids, penicillin, acetic acid, fluoride, nitroglycerine, enzymes, vitamins, antibodies, hormones, and a variety of anesthetics.

Though the electrolytic solution of some iontophoresis system electrode may not include medicament ions, these iontophoresis system electrodes should nevertheless include suitable conductive ions. The conductive ions are needed to support current flow through the iontophoresis system. The conductive ions should be selected so that any conductive ions that are delivered into the body during iontophoresis do not cause deleterious effects within the body. The solvent of the electrolytic solution that is included in any electrode of the iontophoresis system may be any solvent, such as water, that suitably solubilizes medicament ions or conductive ions that are included in the electrolytic solution. Additionally, the solvent of the electrolytic solution should selected to avoid any harmful effects to the body.

Medicament ions formed on dissociation of ionic substances are desirable ions that are intended for delivery into the human or animal body. Complimentary ions formed on dissociation of ionic substances are ions that are not intended for delivery into the human or animal body. Aside from complimentary ions, other ions that are not intended for delivery into the human or animal body are subsequently referred to as adverse ions.

An iontophoresis system (not shown) typically includes two electrodes (not shown) that are in electrical contact with the body. Either or both of the electrodes of the iontophoresis system may have the structure of the electrode 10. One of the electrodes of the iontophoresis system may be characterized as an "active" electrode of the system, and the other electrode may be characterized as a "ground" electrode of the system. One of the electrodes of the iontophoresis system also serves as a positively charged anode and the other electrode is a negatively charged cathode. When one of the electrodes delivers medicament ions to the body, the electrode delivering the medicament ions is the active electrode and the other electrode, the ground electrode, completes the electrical circuit through the body between the active electrode and the ground electrode.

When the anode of the iontophoresis system has the structure of the electrode 10, electrolytic solution is included in the reservoir 12 to support current flow from the terminal 16 through conductive layer 14 and the reservoir 12 and into the body. The electrode 10 that serves as the anode may be either the active electrode for delivering medicament ions into the body or may be the ground electrode. When the cathode of the iontophoresis system has the structure of the electrode 10, electrolytic solution is included in the reservoir 12 to support current flow from the body through the reservoir 12 and the conductive layer 14 and into the terminal 16. The electrode 10 that serves as the cathode may be either the active electrode for delivering medicament ions into the body or may be the ground electrode. Additionally, as explained below, the anode and the cathode that have the structure of the electrode 10 may each serve as both active and ground electrodes when medicament ions are delivered from both the anode and the cathode.

The reservoir 12 consists of a structural matrix that accepts and holds the electrolytic solution of any dissociated ionic substance(s). The electrolytic solution may be introduced into the matrix of the reservoir 12 by a conventional technique, such as by injection with a hypodermic needle. The reservoir 12 may hold the electrolytic solution of medicament ions and complimentary ions both prior to and during use of the electrode to deliver medicament ions into the body. In the electrode 10 of FIG. 1, the wicking layer 18 may also contain the electrolytic solution.

The reservoir 12 and the wicking layer 18 should be sized to ensure that substantially all of the electrolyte solution is held within the reservoir 12 to enhance contact between the pH buffer and the electrolyte solution. At least about 75% of the volume of the electrolytic solution should be held within the reservoir 12. Preferably, at least about 90% of the volume of the electrolytic solution is held in the reservoir 12. In one embodiment of the electrode 10, about 2 milliliters of the electrolytic solution are contained in the combined volume of the reservoir 12 and the wicking layer 18. Together, the reservoir 12 and the wicking layer 18 should contain at least enough medicament ions for one session of patient treatment.

The reservoir 12 of the electrode 10, in addition to holding the electrolytic solution of medicament ions, may also incorporate a pH buffer that is immobilized within the reservoir 12. The pH buffer neutralizes hydrogen ions or hydroxide ions generated by electrolysis of water when current is applied to the iontophoresis system. Hydrogen ions and hydroxide ions are examples of adverse ions that are not intended for delivery into the human or animal body. Additionally, buffering ions, and complimentary ions of the buffering ions, that are formed on dissociation of the pH buffer in the electrolytic solution are examples of adverse ions that are not intended for delivery into the human or animal body.

When the iontophoresis system is buffered to neutralize hydrogen or hydroxide ions generated by electrolysis of water, the pH buffer of the reservoir 12 preferably neutralizes any hydrogen ions or hydroxide ions that are generated in the electrode 10. If the anode of the iontophoresis system is structured like the electrode 10, basic elements included in the reservoir 12 neutralize hydrogen ions generated at the anode. If the cathode of the iontophoresis system is structured like the electrode 10, acidic elements included in the reservoir 12 neutralize hydroxide ions generated at the cathode.

One significant benefit of the present invention is the ability to closely and accurately control the dosage of pH buffer that is included in the electrode 10. For example, the method of the present invention permits a predetermined amount of pH buffer material to be measured and fully incorporated into the structural matrix of the reservoir 12. Existing techniques, such as dipping an electrolyte containment matrix in an aqueous suspension of pH buffer, do not permit adequate control of the quantity of buffer that is associated with the matrix since variables controlling how much buffer sticks to the matrix may change with time. Also, buffer that adheres less strongly to the matrix may be easily abraded or otherwise separated from the matrix. Thus, in order to make electrodes that adequately maintain a safe pH range proximate the skin, it is typically necessary to apply as much as ten times more pH buffer material to existing electrodes than is chemically necessary for the actual neutralization of hydrogen or hydroxide ions.

Another significant benefit of the electrode 10 is that the pH buffer material is immobilized within the structure of the reservoir 12 which prevents losses of pH buffer material from the reservoir 12 during assembly and handling. Immobilization of the pH buffer within the reservoir 12 also prevents losses of buffer ions from the reservoir 12 during use of the electrode 10. In existing iontophoresis systems, pH buffer material that is not secured within the storage matrix may be abraded from or otherwise be separated away from the electrode. This is not a problem with the inventive electrode 10 since the pH buffer material is integrally incorporated within the structure of the reservoir 12. The pH buffer material may even be chemically bonded in place within the reservoir 12. Integral incorporation of pH buffer material prevents movement of pH buffer material within the reservoir 12, or away from the reservoir 12, with the result that the pH buffer material remains uniformly dispersed within the reservoir 12 during use of the electrode 10 in iontophoresis. Uniform dispersal of the pH buffer material in the reservoir 12 helps maintain uniform pH levels along the interface of the electrode 10 and the skin during use of the electrode 10.

Though the reservoir 12 of the electrode 10 may be multi-layered, the reservoir 12 preferably consists of only a single, monolithic layer. Formation of the reservoir 12 as a single layer simplifies the structure and manufacture of the reservoir 12, while maintaining performance benefits of the reservoir 12. The layer, or layers, of the reservoir 12 may generally be made of any permeable material that has suitable absorbent characteristics. Some examples of the permeable material include foamed materials, such as polyurethane foam; woven or knitted fibers and fabrics, such as felt and polyester fleece; and non-woven fabrics.

Permeable materials that are used as the layer(s) of the reservoir 12 should be highly absorbent, should have a relatively large specific absorbency, and should absorb the electrolytic solution at a relatively high rate. High absorbency is needed so that the surface area and weight of the reservoir 12 and the dimensions and weight of the electrode 10 can be minimized without sacrificing the quantity of medicament ions that the electrode 10 is capable of administering. The permeable material needs to have a relatively high rate of absorption so that the electrolytic solution can be quickly placed in the reservoir 12. The relatively high rate of absorption also minimizes or eliminates losses of the electrolytic solution from the electrode 10 during incorporation of the electrolytic solution into the reservoir.

The permeable material should be capable of absorbing at least about 600 milliliters of electrolytic solution per square meter of permeable material surface area. Preferably, the permeable material should be capable of absorbing at least about 1000 milliliters of electrolytic solution per square meter of permeable material surface area. More preferably, the permeable material should be capable of absorbing at least about 2000 milliliters of electrolytic solution per square meter of permeable material surface area.

For purposes of determining absorbency, the surface area of the permeable material is determined after the permeable material has been formed into the layer(s) of the reservoir 12. Each layer will have major surfaces and minor surfaces. Since the thickness dimension of each layer will typically be orders of magnitude less than the length and width dimensions, the diameter dimension, or other dimension of the layer, the minor surfaces are defined as those surfaces that encompass the thickness of the layer, and the major surfaces are defined as those surfaces that do not encompass the thickness of the layer. Where the reservoir 12 includes multiple layers of the permeable material, each of the layers should have essentially the same major surface dimensions so that each layer is essentially coextensive with the other layers. Though the layers do not necessarily need to have the same thickness, the layers preferably do have substantially the same thickness. The absorbency of the permeable material may be determined by applying the electrolytic solution to any major surface of any layer of permeable material. The surface area of the permeable material, for purposes of evaluating absorbency, is the surface area of the major surface to which the electrolytic solution is applied.

Also, the permeable material should have a relatively high specific absorbency of at least about 0.5 milliliters of electrolytic solution per gram of permeable material. Preferably, specific absorbency of the permeable material should be at least about 1.0 milliliters of electrolytic solution per gram of permeable material. More preferably, the specific absorbency of the permeable material should be at least about 3.0 milliliters of electrolytic solution per gram of permeable material.

Furthermore, about 3 milliliters of the electrolytic solution should be absorbed into 1 gram of the permeable material in less than about 3 minutes. Preferably, about 3 milliliters of the electrolytic solution should be absorbed into 1 gram of the permeable material in less than about 1 minute. More preferably, about 3 milliliters of the electrolytic solution should be absorbed into 1 gram of the permeable material in less than about 10 seconds.

The permeable material may generally be or incorporate any pH buffer material in any form. For example, the permeable material may be or incorporate ion-exchange material, such as ion-exchange material that is organic in chemical structure. Thus, the permeable material may be or incorporate anionic or cationic ion-exchange material. Additionally, the permeable material may incorporate or consist of anionic and cationic ion-exchange materials or amphoteric ion-exchange material. This permits interchangeable use of the electrode 10 as the anode or the cathode of the iontophoresis system or, alternatively, as the anode and the cathode of the iontophoresis system.

The pH buffer material, such as the ion-exchange material should be capable of maintaining the pH of the electrolytic solution within a range of from about 4 to about 8 to avoid irritating or burning the skin. For example, the pH buffer material should be capable of holding about 0.1 milliequivalents of acid or about 0.1 milliequivalents of base while maintaining the about 4 to about 8 pH range of the electrolytic solution. Preferably, the pH buffer material is capable of holding about 0.1 milliequivalents of acid and about 0.1 milliequivalents of base while maintaining the about 4 to about 8 pH range of the electrolytic solution.

The pH buffer material should also have a relatively high buffering capacity to aid in minimizing the size and weight of the reservoir 12 while maintaining the about 4 to about 8 pH range of the electrolytic solution during iontophoresis periods on the order of about 40 minutes or more. At a minimum, the buffering capacity of the pH buffer material should be at least about 0.5 milliequivalents of acid or base per gram of pH buffer material. Preferably, the buffering capacity of the pH buffer material should be at least about 1.0 milliequivalents of acid or base per gram of pH buffer material More preferably, the buffering capacity of the pH buffer material should be at least about 1.5 milliequivalents of acid or base per gram of pH buffer material. Still more preferably, the buffering capacity of the pH buffer material should be at least about 1.5 milliequivalents of acid per gram of pH buffer material and at least about 1.5 milliequivalents of base per gram of pH buffer material.

The ion-exchange material may consist of ion-exchange functionalities that are chemically bonded to the permeable material. Examples of suitable ion-exchange materials include any homogeneous ion-exchange material, such as ion-exchange polymer and ion-exchange copolymer. In homogeneous ion-exchange material, one or more different ion-exchange functionalities are chemically bonded to the homogeneous ion-exchange material.

One type of ion-exchange copolymer consists of the reaction product of a first prepolymer and a second prepolymer. The first prepolymer may generally be any monomeric precursor or a mixture of different monomeric precursors. The second prepolymer may generally be any monomeric ionexchange precursor or a mixture of different monomeric ion-exchange precursors. Monomeric ion-exchange precursor may be formed by attaching one or more ion-exchange functional groups to any monomeric precursors using any conventional chemical bonding technique, such as substitution or grafting. At least one of the monomeric precursors that acts as the first prepolymer and at least one of the monomeric precursors that is used in forming the monomeric ion-exchange precursor should be different from each other. Another type of ion-exchange copolymer consists of a graft ion-exchange copolymer where one or more ion-exchange functionalities are chemically grafted or substituted onto a core copolymer. One type of ion-exchange polymer consists of a graft ion-exchange polymer where one or more ion-exchange functionalities are chemically grafted or substituted onto a core polymer.

Alternatively, the ion-exchange material may be physically entrapped within the permeable material. The molecular weight of any ionexchange material that is physically entrapped in the permeable material should be at least about 5000 daltons (grams per mole) to immobilize the ion-exchange material in the permeable material. As an example, the ion exchange material may be any heterogeneous ion-exchange material, such as heterogeneous ionexchange foam. Heterogeneous ion-exchange foam includes at least two distinct phases. For any electrode that includes the heterogeneous ion-exchange foam, each of the phases should be insoluble in the solvent portion of any electrolytic solution included in the electrode to immobilize physical movement of any component of the heterogeneous ion-exchange foam within the electrode. The phases may each be solid or semi-solid in nature. Alternatively, some phase(s) may be solid in nature, and other phase(s) may be semi-solid in nature. One or more organic ion-exchange substances make up one or more of the phases, and polymer foam or copolymer foam makes up the other phase(s).

Heterogeneous ion-exchange foam is made by dispersing one or more organic ion-exchange substances in one or more prepolymer components of polymer or copolymer foam, prior to reacting the prepolymer components to make the polymer or copolymer foam. After formation of the heterogeneous ion-exchange foam, the polymer or copolymer foam and the organic ionexchange substance(s) form the distinct phases of the heterogeneous ion-exchange foam. In the heterogeneous ion-exchange foam, the organic ion-exchange substance(s) are physically entrapped within the structure of the polymer or copolymer foam. Preferably, the polymer or copolymer foam portion of the heterogeneous ion-exchange foam is an open cell foam that supports enhanced movement within the heterogeneous ion-exchange foam of any medicament ion included in the electrolytic solution.

Other examples of heterogeneous ion-exchange materials include various composite polymer mixtures of host polymeric material and organic ionexchange functionality. The host polymeric material may be formed as a gel, a membrane, a hydrocolloid, a membrane, a laminate, particles, granules, or other suitable matrix. The ion-exchange functionality may be dispersed within the host polymeric material, such as by impregnating the ion-exchange functionality within the host polymeric material either before or after formation of the host polymeric material. In this form, the ion-exchange functionality is physically entrapped within the host polymeric material. The molecular weight of any ionexchange material that is incorporated in host polymeric material should be at least about 5000 daltons (grams per mole) to immobilize the ion-exchange material in the host polymeric material. The ion-exchange finctionality may also be coated onto the host polymeric material. WVhen the host polymer material is a loose material, such as in the form of particles or granules, the reservoir 12 may include suitable boundary layers (not shown) for containing the host material within the reservoir 12.

Alternatively, the permeable material of the reservoir 12 may be or may include a proton sponge. The proton sponge, which may serve as the pH buffer, is essentially an effective base compound that exhibits weak nucleophilic character. Proton sponges exhibit weak nucleophilic characteristics due to steric effects that are present within the proton sponge. The steric effects influence ionic reactions of the proton sponge and contribute to the weak nucleophilic character. The weak nucleophilic character causes the proton sponge to exhibit minimal electron donation tendencies.

Steric effects exist in proton sponges for a variety of reasons, including the spacing between adjacent groups that are attached to the proton sponge, and the shape of the proton sponge. Proton sponges, however structured, are referred to as "proton sponges" because of the extremely high affinity of the underlying structure for protons. In this application, including the specification and the claims, proton sponge is to be understood as referring to any compound that is capable of trapping protons without consequent release of any other ion(s), including, but not limited to compounds, that are characterized in this application as proton sponges or analogues of proton sponges.

One benefit of the present invention is the ability to closely and accurately control the dosage of proton sponge material, such as proton sponge functional groups, that is included in the electrode 10. Homogeneous incorporation of proton sponge functional groups into the layer(s) of the reservoir 12, such as by chemical bonding, secures the proton sponge functional groups within the structural matrix of the reservoir 12 and prevents losses of proton sponge functional groups from the reservoir 12 during assembly, handling, and use of the electrode. When the proton sponge material is heterogeneously incorporated in the layers of the reservoir 12, the molecular weight of the proton sponge material should be at least about 5000 daltons (grams per mole) to immobilize the proton sponge material in the reservoir 12.

Although the permeable material may be or may incorporate any suitable proton sponge, three particular types of proton sponges are illustrative of proton sponges that may be incorporated in the permeable material. A first type of proton sponge, subsequently referred to as "Type A" proton sponge, may be characterized as an organic carrier compound that includes one or more attached proton sponge functional groups. Each proton sponge functional group consists of a neighboring pair of proton sponge functional group components. In the Type A proton sponge, an inorganic component or atom, such as nitrogen, of each proton sponge functional group component is attached to, but is not a part of, the carrier compound. One example of the Type A proton sponge is 1,8-Bis(diethylamino)-2,7-dimethoxynaphthalene, which has the following structure:

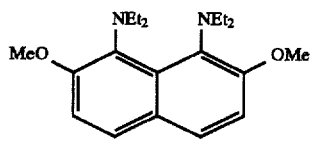

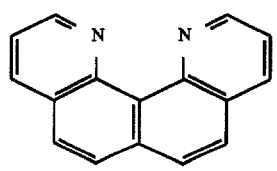

For 1,8-Bis(diethylamino)-2,7-dimethoxynaphthalene, the carrier compound is 2,7-dimethoxynaphthalene and the diethylamino groups are the proton sponge functional group components. Together, the two diethylamino groups form the proton sponge functional group. In the Type A proton sponge, close spacing of the neighboring proton sponge functional group components hinders movement of reactants toward the proton sponge. Taking 1,8-Bis(diethylamino)-2,7-dimethoxynaphthalene as an example, the close spacing of the two diethylamino groups forces the lone pair of nitrogens near each other and creates steric strain in the proton sponge. Protonation of sterically strained proton sponges, such as addition of hydrogen ion between adjacent strained nitrogens, relieves the strain between the nitrogens, stabilizes the Type A proton sponges, and enables further ionic reaction of the protonated Type A proton sponges.

For example, in 1,8-Bis(diethylamino)-2,7-dimethoxynaphthalene, resonant covalent bonding of hydrogen to the nitrogens of the respective proton sponge functional group components, along with resonant hydrogen bonding between hydrogen and the nitrogens of the respective proton sponge functional group components, relieves the strain between the lone pair of nitrogens and stabilizes the proton sponge. At any particular point in time, the hydrogen may be covalently bonded to the nitrogen of one of the proton sponge functional group components and may form a hydrogen bond with the nitrogen of the other proton sponge functional group component. Due to the resonant nature of the covalent bonding and the hydrogen bonding, at a different point in time, a hydrogen bond may exist where a covalent bond formerly existed between the hydrogen and the nitrogen of the one of the proton sponge functional group components, and a covalent bond may exist where a hydrogen bond formerly existed between the hydrogen and the nitrogen of the other proton sponge functional group component.

A second type of proton sponge, subsequently referred to as a "Type B" proton sponge, may be characterized either as (1) a heterocyclic compound that includes at least one pair of hetero atoms or as (2) a straight or branched organic chain that includes at least one pair of hetero atoms in the chain. Subsequent references to "organic core compound" are to be understood as referring (1) to the heterocyclic compound, of the Type B proton sponge, that includes at least one pair of hetero atoms or as referring (2) to the straight or branched organic chain, of the Type B proton sponge, that includes at least one pair of hetero atoms in the chain. In the Type B proton sponge, each of the hetero atoms is substituted in the organic core compound in place of carbon. One example of the Type B proton sponge is quino[7,8-h] quinoline, which has the following structure:

In quino[7,8-h]quinoline, nitrogen is substituted in place of carbon at one position in each of the two organic rings of the organic core compound. In the Type B proton sponge, the shape of the organic core compound places the pair of hetero atoms relatively close together and hinders movement of reactants toward the pair of hetero atoms. Taking quino[7,8-h] quinoline as an example, the shape of the organic core compound places the pair of nitrogens near each other and hinders movement of reactants toward the nitrogens. Protonation of Type B proton sponges, such as addition of hydrogen ion between adjacent hetero atoms, stabilizes the Type B proton sponges and enables further ionic reaction of the protonated Type B proton sponge. For example, in quino[7,8-h] quinoline, resonant covalent bonding of hydrogen to one of the heterocyclic nitrogen along with resonant hydrogen bonding between hydrogen and the other of the heterocyclic nitrogens stabilizes the Type B proton sponge and enables further ionic reaction of the protonated quino [7,8-h] quinoline. At any particular point in time, the hydrogen may be covalently bonded to one of the heterocyclic nitrogens of the proton sponge and may form a hydrogen bond with the other heterocyclic nitrogen of the proton sponge. Due to the resonant nature of the covalent bonding and the hydrogen bonding, at a different point in time, a hydrogen bond may exist where a covalent bond formerly existed between the hydrogen and one of the heterocyclic nitrogens of the proton sponge, and a covalent bond may exist where a hydrogen bond formerly existed between the hydrogen and the other of the heterocyclic nitrogens of the proton sponge.

A third type of proton sponge, subsequently referred to as a "Type C" proton sponge, may be characterized as (1) a heterocyclic compound that includes at least one hetero atom or may be characterized as (2) a straight or branched organic chain that includes at least one hetero atom in the chain. Subsequent references to "organic support compound" are to be understood as referring to (1) the heterocyclic compound, of the Type C proton sponge, that includes at least one hetero atom or to (2) the straight or branched organic chain, of the Type C proton sponge, that includes at least one hetero atom in the chain. The hetero atom is substituted into the organic support compound in place of carbon and at least two organic groups are attached to carbons of the organic support compound that are located adjacent to the hetero atom. Also, in the Type C proton sponge, one of the two organic groups is attached to a carbon that is on one side of the hetero atom, and the other of the two organic groups is attached to a carbon that is on the other side of the hetero atom. Thus, the two organic groups are attached to carbons that are located on opposing sides of the hetero atom. One example of the Type C proton sponge is 2,6-di-t-butyl pyridine, which has the following structure:

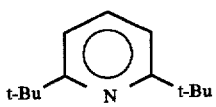

In 2,6-di-t-butylpyridine, nitrogen is substituted in place of carbon at one position in the organic ring. Also, two t-butyl groups are attached to ring carbons located next to the ring nitrogen so that the t-butyl groups are located on opposing sides of the ring nitrogen.

In the Type C proton sponge, the bulky nature of the organic groups that are attached on opposing sides of the hetero atom hinders movement of reactants toward the hetero atom. For example, in 2,6-di-t-butylpyridine, the t-butyl groups attached on opposing sides of the ring nitrogen hinder movement of reactants toward the ring nitrogen. Protonation of Type C proton sponges, such as addition of hydrogen ion to the hetero atom, stabilizes the Type C proton sponges and enables further ionic reaction of the protonated Type C proton sponge. For example, in 2,6-di-t-butyl pyridine, covalent bonding of hydrogen to the ring nitrogen stabilizes the proton sponge and enables further ionic reaction of the protonated 2,6-di-t-butylpyridine.

It has been discovered that proton sponges are capable of accepting hydrogen ions ($H^+$) that are generated by electrolysis of water at the anode during iontophoretic delivery of medicament ions, such as lidocaine hydrochloride. More specifically, it has been found that proton sponges, unlike ion-exchange compounds, are capable of scavenging hydrogen ions ($H^+$) that are generated at the anode during iontophoretic delivery of medicament ions, without releasing any ions. Ion-exchange compounds, by definition, exchange ions and thus accept ions and release ions during ion-exchange reactions. Proton sponges, by virtue of this scavenging characteristic, are capable of acting as ion scavengers that accept hydrogen ions without releasing any adverse ions that will compete with medicament ions for delivery to the body. Besides lidocaine hydrochloride, examples of other ionic substances that may be advantageously administered at the anode in the presence of the proton sponge include papaverine hydrochloride, morphine hydrochloride, pilocarpine hydrochloride, ephedrine hydrochloride, lignocaine hydrochloride, cetylpyridinium chloride, chloroprocaine hydrochloride, chlortetracycline hydrochloride, imipramine hydrochloride, etc.

As noted, permeable material may be used to make the layer(s) of the reservoir 12 that is depicted in FIG. 1. Any layer(s) of the permeable material may be or may incorporate homogeneous ion-exchange material or heterogeneous ion-exchange material. Alternatively, any layer(s) of the permeable material may incorporate or may consist entirely of proton sponge. Furthermore, any layer(s) of the permeable material may include homogeneous ion-exchange material, heterogeneous ion-exchange material, and/or proton sponge, in any combination and in any ratio.

Continuing with FIG. 1, the conductive layer 14 of the electrode conducts current that is applied to the terminal 16 and distributes the current across an inner surface 22 of the reservoir 12. The conductive layer 14 should uniformly distribute current across the inner surface 22. Preferably, the current density proximate the interface of the electrode 10 and the skin does not exceed about 0.5 milliamperes per square centimeter. Current densities proximate the skin of higher than about 0.5 milliamperes per square centimeter increase the likelihood of patient discomfort and irritation of the skin.

The conductive layer 14 may be formed of any suitable conductive material. Preferably, the conductive layer 14 is highly conductive and has a maximum resistivity of about 10 ohms cm to enhance the efficiency of the electrode 10. The conductive layer 14 should also be flexible so the electrode can closely conform to the shape of the skin. To prevent degradation of the electrochemical characteristics of the electrode 10, the conductive layer 14 should be impermeable to fluids, such as the electrolytic solution contained in the electrode 10. Examples of suitable materials for the conductive layer include thin sheets of carbon-loaded silicon rubber, metal foil, conductive cloth, or conductive adhesive.

The wrap 18 of the electrode 10 aids in holding the reservoir 12 and the conductive layer 14 together. When the electrode 10 is placed against the skin, the wrap 18 is in contact with the body and separates the reservoir 12 from the body. One use of the electrode 10 is to transfer medicament ions derived from ionic substances, such as medications, drugs, or other therapeutic chemicals, through the skin and into the body. Therefore, the wrap 18 should act as a wick that negligibly, if at all, restricts flow of medicament ions from the reservoir 12 to the body.

Examples of suitable materials for the wrap 18 include non-woven blends of polyester and cellulose, such as Durx® 670 or Durx® 770, which are available from Berkshire Corporation of Great Barrington, Mass. Other examples of suitable materials for the wrap 18 include blends of cellulose and polyethylene terephthalate, such as Unilayer® 1+2 or Unispun® 200, which are available from Midwest Filtration Company of Fairfield, Ohio Still further examples of suitable materials for the wrap 18 include various non-woven and interlining fabrics available from Hollingsworth & Vose Company of Floyd, Va.

The adhesive covering 20 is an adhesive tape that serves as a structural support component of the electrode 10 and is also useful for securing the electrode 10 to the skin. The adhesive covering 20 also prevents seepage of electrolytic solution along the skin away from the electrode 10. The adhesive covering 20 should be highly flexible so that the covering readily conforms to the skin. The adhesive covering 20 may be formed of any suitable material, such as a thin layer of polyvinyl chloride foam that is coated with pressuresensitive adhesive. It is to be understood that other suitable flexible materials that are coated with adhesive may be used to form the adhesive covering 20.

Throughout the drawings, like elements are referred to using like reference characters.

Figure 2:
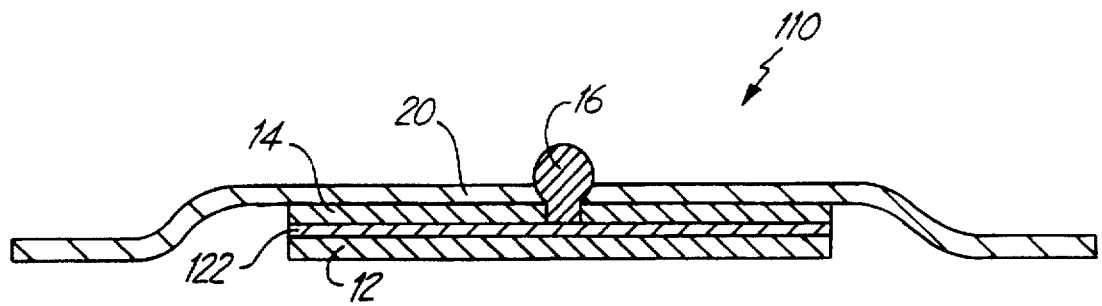
FIG. 2 is a sectional view of another pH buffered electrode of the present invention.

The electrode 10 may be modified to form an electrode 110, as in FIG. 2, by replacing the wicking wrap 18 of the electrode 10 with a conductive adhesive layer 122. In the electrode 110, the conductive adhesive layer 122 is placed between and in contact with the reservoir 12 and the conductive layer 14. The function of the conductive adhesive layer 122, similar to the function of the wrap 18, is to aid in holding the reservoir 12 and the conductive layer 14 together. With this structure, the reservoir 12 of the electrode 110 is in direct contact with the body when the electrode 110 is placed against the body.

To prevent degradation of the electrochemical characteristics of the electrode 110, the conductive adhesive layer 122 should be impermeable to the electrolytic solution that is held in the reservoir 12. Examples of suitable impermeable materials for use as the conductive adhesive layer 122 include any of the ARCLAD 8000 series adhesives available from Adhesive Research, Inc. of Glen Rock, Pa; VERA-TEC adhesive, available from Con-Med Corporation of Utica, N.Y.; Type CMI 107-25 carbon and silver filled acrylic adhesive, available from Creative Materials, Inc. of Tyngsboro, Mass.; and Type 102-32 silicone-based adhesive, also available from Creative Materials, Inc.

When used in the electrode 110, the reservoir 12 accepts and holds the electrolytic solution. In the electrode 110, only the reservoir 12 contains electrolytic solution. The reservoir 12 of the electrode 110 may hold the electrolytic solution both prior to and during use of the electrode 110 to deliver any medicament ions through the skin and into the body of the patient. When used in the electrode 110, the reservoir 12 should contain at least enough of the medicament ions for one session of patient treatment.

Figure 3:
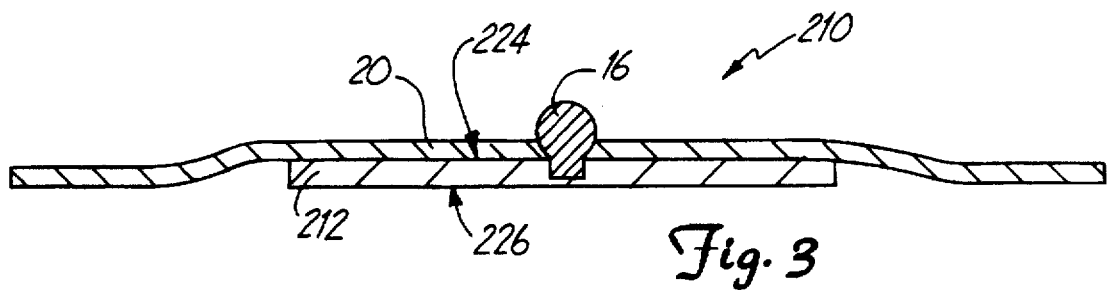
FIG. 3 is a sectional view of another pH buffered electrode of the present invention.

Alternatively, the electrode 10 may be modified to form an electrode 210, as depicted in FIG. 3. The electrode 210 includes only a reservoir 212 between the adhesive cover 20 and the body. The electrode 210, as compared to the electrode 10 of FIG. 1, does not include the conductive layer 14 or the wicking wrap 18. The electrode 210, as compared to the electrode 110 of FIG. 2, does not include the conductive layer 14 or the conductive adhesive layer 122. When the electrode 210 is placed against the skin, the reservoir 212 is in direct contact with the skin.

The reservoir 212 accepts and holds the electrolytic solution. The reservoir 212 may hold the electrolytic solution both prior to and during use of the electrode to deliver any medicament ions through the skin of the patient. In the electrode 210, only the reservoir 212 contains electrolytic solution. The reservoir 212 should contain at least enough medicament ions for one session of patient treatment.

It should be understood that both electrodes (not shown) of the iontophoresis system (not shown) may have the structure of the electrode 10, the electrode 110, or the electrode 210. Alternatively, either of the two electrodes of the iontophoresis system may have, in any combination, the structure of the electrode 10, the structure of the electrode 110, the structure of the electrode 210 or a structure that is different from that of the electrode 10, the electrode 110, and the electrode 210. For example, one of the electrodes of the iontophoresis system may have the structure of the electrode 10 and the other electrode of the iontophoresis system may have the structure of the electrode 210. As another example, one of the electrodes of the iontophoresis system may have the structure of the electrode 110 and the other electrode of the iontophoresis system may have a structure that is different from the structure of the electrode 10, the electrode 110, and the electrode 210.

No matter whether the wrap 18 or the conductive adhesive layer 122 is used, the electrode 10 and the electrode 110 are each simpler in construction than existing electrodes. For example, some existing electrodes include four separate components between an adhesive attachment component and the skin, whereas the electrode 10 and the electrode 110 include only three separate components between the adhesive cover and the skin. The electrode 210 of FIG. 3 is even simpler than the electrode 10 and the electrode 110 depicted in FIGS. 1 and 2, respectively, since the electrode 210 of FIG. 3 includes only one component between the adhesive cover 20 and the skin.

The reservoir 212 has the same compositional and structural features as the reservoir 12, with the exception that carbonized particles are incorporated and immobilized in the reservoir 212 to make the reservoir 212 conductive. In the electrode 210, the conductive terminal 16 is attached to the reservoir 212 to direct current flow into the reservoir 212. The reservoir 212 conducts current that is applied to the terminal 16. The current in the reservoir 212 provides the motive force that drives the medicament ions in the reservoir 212 into the body.

The carbonized particles, such as conductive forms of carbon black, may be homogeneously incorporated throughout the reservoir 212. Additionally, the carbonized particles should have a shape and size that is adequate to immobilize the carbonized particles within the reservoir 212. When the carbonized particles are homogeneously incorporated in the reservoir 212, the incorporation should be accomplished so that the impedance of the reservoir 212 substantially matches the impedance of the skin. If the impedance of the reservoir 212 does not substantially match the impedance of the skin, electrical irritation or burning of the skin may result from use of the reservoir 212 that includes homogeneously incorporated carbonized particles.

Alternatively, the carbonized particles may be incorporated in the reservoir 212 of the electrode 210 to create an electric potential between an upper surface 224 and a lower surface 226 of the reservoir 212. The carbonized particles should have a shape and size that is adequate to immobilize the carbonized particles within the reservoir 212. If the anode of the iontophoresis system is structured like the electrode 210, the electric potential should decrease between the surface 224 and the surface 226. If the cathode of the iontophoresis system is structured like the electrode 210, the electric potential should increase between the surface 224 and the surface 226. The carbonized particles may be distributed within the reservoir 212 or concentrated proximate the upper surface 224, as appropriate, to generate the change in potential needed for the anode and the cathode to function in the iontophoresis system. The carbonized particles should not be concentrated proximate the lower surface 226 of the reservoir 212, since such concentration proximate the lower surface 226 would create an impedance gradient between the lower surface 226 and the skin that may cause electrical irritation or burning of the skin.

Current entering the reservoir 212 should be uniformly distributed across the reservoir 212. Preferably, the current density proximate the interface of the reservoir 212 and the skin does not exceed about 0.5 milliamperes per square centimeter. Current densities proximate the skin of higher than about 0.5 milliamperes per square centimeter increase the likelihood of patient discomfort and irritation of the skin.

The reservoir 212 of the electrode 210 may be formed of any suitable material, such as the permeable material of the reservoir 12. Preferably, the permeable material used to form the reservoir 212 includes or consists entirely of the proton sponge, such as the heterogeneous proton sponge foam, or the ion-exchange material, such as the ion-exchange copolymer or the heterogeneous ion-exchange foam. Thus, the reservoir 212 preferably includes pH buffer material that is immobilized within the reservoir 212 and that is capable of neutralizing hydrogen ions or hydroxide ions generated by electrolysis of water in the iontophoresis system. Alternatively, the permeable material used to form the reservoir 212 may consist of or incorporate any combination of the ionexchange material and the proton sponge. It is to be understood that any ionexchange material and/or proton sponge that is included in the layer(s) of the reservoir should be immobilized in the layer(s) to prevent movement of any included ion-exchange material or proton sponge within the reservoir 212.

When the electrode 210 is incorporated in the iontophoresis system (not shown) and is buffered to neutralize adverse ions generated during electrolysis of water, the reservoir 212 incorporates the pH buffer that neutralize any hydrogen ions or hydroxide ions generated in the reservoir 212. If the anode of the iontophoresis system is structured like electrode 210, basic elements included in the reservoir 212 neutralize hydrogen ions generated at the anode. Conversely, if the cathode of the iontophoresis system is structured like the electrode 210, acidic elements included in the reservoir 212 neutralize hydroxide ions generated at the cathode.

All subsequent statements about the electrode 10 apply equally to the electrode 110 and the electrode 210, unless otherwise indicated. Also, all subsequent statements about the reservoir 12 apply equally to the reservoir 212, unless otherwise indicated.

Though prior comments about the iontophoresis system mention delivery of medicament ions from one or the other of the electrodes that is structured like the electrode 10, both iontophoresis system electrodes may be used to deliver medicament ions. When each electrode of the iontophoresis system delivers medicament ions to the body, those skilled in the art will readily recognize that each electrode of the iontophoresis system acts as the active electrode for the respective medicament ions delivered from the respective electrode of the iontophoresis system. Similarly, each electrode of the iontophoresis system acts as the ground electrode for the respective electrode of the iontophoresis system that is delivering medicament ions to the body.

One necessary step in making the electrode 10 is to obtain the permeable material that is used to make the reservoir 12. As noted, one type of ion-exchange copolymer may be formed by reacting a first prepolymer and a second prepolymer. The first and second prepolymers may be polymerized to form the ion-exchange copolymer using any conventional copolymerization technique that is suitable for polymerizing prepolymers that are used to make the copolymer. The first prepolymer may consist of a single monomeric precursor or may consist of a mixture of different monomeric precursors. Examples of monomeric precursors suitable for use as the first prepolymer include alkanes, alkenes, and substituted benzenes, such as divinyl benzene.

The second prepolymer may generally be any single monomeric ion-exchange precursor or a mixture of different monomeric ion-exchange precursors. Monomeric ion-exchange precursors may be formed by attaching one or more ion-exchange functional groups to any monomeric precursors using any conventional chemical bonding technique, such as substitution or grafting. At least one of the monomeric precursors that acts as the first prepolymer and at least one of the monomeric precursors that is used in forming the monomeric ion-exchange precursor should be different from each other.

Examples of monomeric precursors suitable for use in making the monomeric ion-exchange precursor include substituted benzenes, such as divinyl benzene. Other examples of monomeric precursors suitable for use in making the monomeric ion-exchange precursor include a variety of urethanes, which may be include a variety of different functional groups, such as (1) diol groups and diisocyanate groups and (2) triol groups and tri-isocyanate groups. Examples of ion-exchange functional groups that are suitable for attachment to the monomeric precursor(s) include carboxyl groups, amino groups, —$SO_3H$ groups, —$OPO_3H_2$ groups. Thus, some examples of the monomeric ion-exchange precursor, i.e. the second prepolymer, are acrylic acid and methacrylic acid.

One suitable ion-exchange copolymer is prepared by copolymerizing divinyl benzene, which serves as the first prepolymer, and methacrylic acid, which serves as the second prepolymer. One suitable copolymer of methacrylic acid and divinyl benzene is represented by structural formula I below:

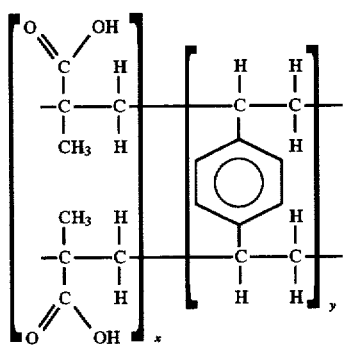

I.

One example of the methacrylic acid/divinyl benzene copolymer with formula I structure is Amberlite® IRP-64, which is available from Rohm & Haas Co. of Philadelphia, Pa. Amberlite® IRP-64 has an x/y ratio of 12. Thus, an average monomer unit of the Amberlite® IRP-64 copolymer has 24 methacrylic acid groups per divinyl benzene group. Additionally, the Amberlite® IRP-64 copolymer is about 4.5% by weight divinyl benzene and about 95.5% by weight methacrylic acid. The Amberlite® IRP-64 copolymer may be part or all of the permeable material used to form the reservoir 12 when the cathode of the iontophoresis system has the structure of the electrode 10.

When the anode of the iontophoresis system has the structure of the electrode 10, the permeable material of the reservoir 12 may be or may include a metal salt of the ion-exchange copolymer. The ion-exchange copolymer may be treated with a mineral acid, such as potassium chloride, to obtain the metal salt of the ion-exchange copolymer. Treatment of the copolymer of graphic formula I with potassium chloride yields the compound represented by graphic formula II, which is one example of a suitable metal salt of the ion-exchange copolymer:

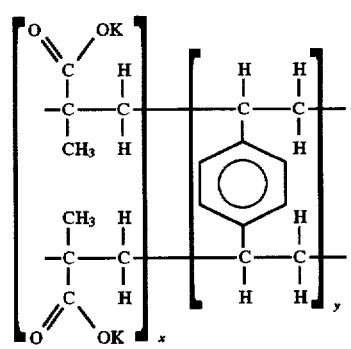

II.

One example of the copolymer metal salt with the formula II structure is Amberlite® IRP-88, which is available from Rohm & Haas Co. Amberlite® IRP-88 has an x/y ratio of 12. Thus, an average monomer unit of the Amberlite® IRP-88 copolymer has 24 metal salt groups of methacrylic acid per divinyl benzene group. The Amberlite® IRP-88 copolymer may be part or all of the permeable material of the reservoir 12 when the anode of the iontophoresis system has the structure of the electrode 10.

One preferred formulation of the ion-exchange copolymer is a urethane/methacrylic acid copolymer with the structure represented in graphic formula III:

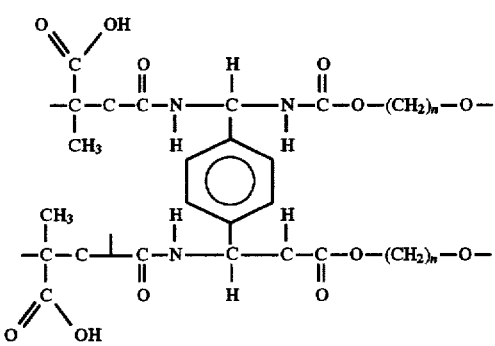

One suitable urethane/methacrylic acid copolymer with the structure of formula III may be manufactured by copolymerizing methacrylic acid with a suitable polyurethane prepolymer, such as a foamable polyurethane prepolymer that is derived from toluene diisocyanate. Methacrylic acid may be obtained from Ashland Chemical Company of St. Paul, Minn. or from Rohm & Haas Co. of Philadelphia, Pa. Foamable polyurethane prepolymer that is derived from toluene diisocyanate is marketed as part of the Hypolb group of products by W. R Grace & Company of Woburn, Mass. Some examples of suitable Hypol® polyurethane prepolymers include Hypol® FHP 2000, Hypol® FHP 2002, and Hypol® FHP 3000.

The urethane/methacrylic acid copolymer with the structure of formula III is preferably from about 65% to about 85% by weight urethane and from about 15% to about 35% by weight methacrylic acid. The urethane/methacrylic acid copolymer with the structure of formula III may be part or all of the permeable material used to form the layer(s) of reservoir 12 when the cathode of the iontophoresis system has the structure of the electrode 10.

When the anode of the iontophoresis system has the structure of the electrode 10, the permeable material of the reservoir 12 may be or may include a metal salt of the urethane/methacrylic acid copolymer of Formula III. One suitable salt of the urethane/methacrylic acid copolymer of Formula III has the structure of graphic formula IV:

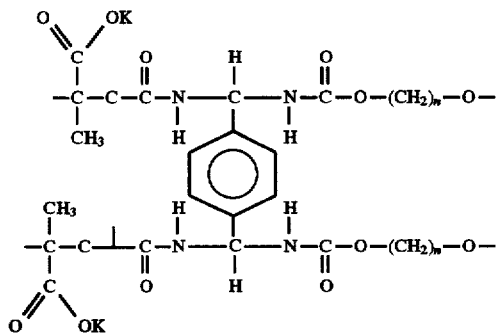

The salt with the structure of graphic formula IV may be formed by treating the urethane/methacrylic acid copolymer of graphic formula III with a suitable mineral acid, such as potassium chloride. Preferably, the mineral acid treatment converts from about 25% to about 45%, by weight, of the carboxylic functionalities of the formula III urethane/methacrylic acid copolymer to the copolymer metal salt of formula IV.

Another preferred formulation of the ion-exchange copolymer is urethane/carboxylic acid copolymer. Suitable urethane/carboxylic acid copolymer may be manufactured by copolymerizing polyacrylic acid prepolymer or polycarboxylic acid prepolymer with a suitable polyurethane prepolymer, such as the foamable polyurethane prepolymer that is derived from toluene diisocyanate. Suitable polyacrylic acid prepolymer and suitable polycarboxylic acid prepolymer are marketed as part of the Tamol®, Acusol®, and Acumer® product groups by Rohm & Haas Co. of Philadelphia, Pa. Some examples of suitable Tamol® prepolymers include Tamol® 850, Tamol® 960, Tamol® 963, and Tamol® 983. Some examples of suitable Acusol® prepolymers include Acusol® 445 and Acusol® 445N. One example of a suitable Acumer® prepolymer is Acumer® 1510. As mentioned, foamable polyurethane prepolymer that is derived from toluene diisocyanate is marketed as part of the Hypol® group of products by W. R Grace & Company of Woburn, Mass.

When the anode of the iontophoresis system has the structure of the electrode 10, the permeable material of the reservoir 12 may be or may include a metal salt of the urethane/carboxylic acid copolymer. The metal salt of the urethane/carboxylic acid copolymer may be formed by treating the urethane/carboxylic acid copolymer with a suitable mineral acid, such as potassium chloride. Preferably, the mineral acid treatment converts from about 25% to about 45%, by weight, of the carboxylic functionalities of the urethane/carboxylic acid copolymer to the metal salt form of the urethane/carboxylic acid copolymer.

As noted, the permeable material of the reservoir 12 may also be formed from or may include heterogeneous ion-exchange foam. The heterogeneous ion-exchange foam should preferably have a uniform pH ranging from about 4 to about 8 to avoid irritating or burning the skin. The heterogeneous ion-exchange foam includes the polymer or copolymer foam portion and one or more organic ion-exchange substances that are dispersed in the polymer or copolymer foam portion. The molecular weight of any organic ion-exchange substances that are incorporated in the polymer or copolymer foam portion should be at least about 5000 daltons (grams per mole) to immobilize the organic ion-exchange substance(s) in the heterogeneous ion-exchange foam.

The organic ion-exchange substances are dispersed in one or more prepolymer components of the polymer foam or the copolymer foam prior to reacting the prepolymer components to make the polymer or copolymer foam. After formation of the heterogeneous ion-exchange foam, the polymer or copolymer foam and the organic ion-exchange substance(s) form distinct phases of the heterogeneous ion-exchange foam. Additionally, the organic ion-exchange substance(s) are physically entrapped within the structure of the polymer or copolymer foam.

Examples of suitable ion-exchange substances, for use in making the heterogeneous ion-exchange foam, include various anion and cation exchange resins, in either gel or macroreticular form, such as the Amberlite® series of resins and the Duolite® series of resins available from Rohm & Haas Corporation and the Dowex® series of resins available from Dow Corporation of Midland, Mich. Examples of suitable Amberlite® resins include Amberlite® IRP-64, Amberlite® IRP-68, Amberlite® IRP-88, Amberlite® CG-50 and Amberlyst®A21. Examples of suitable Duolite® resins include Duolite® C433, Duolite® A-368, and Duolite® A-392S. Examples of suitable Dowex® resins include Dowex® WGR, Dowex® WGR-Z, and Dowex® MWA-1. To aid in attaining the about 4 to about 8 pH range in the heterogeneous ion-exchange foam, the ion-exchange resin should preferably be either weakly basic or acidic, be of fine particle size, and be pharmaceutical-grade gel-type resin.

Examples of prepolymer that are suitable for use in making heterogeneous ion-exchange foam include polyurethane prepolymer, polyester prepolymer, and polystyrene prepolymer. One example of a suitable polyurethane prepolymer is foamable polyurethane prepolymer that is derived from toluene diisocyanate. Suitable examples of the foamable toluene diisocyanate-derived polyurethane prepolymer include prepolymers of the Hypol® series that are available from W. R Grace & Company of Woburn, Mass. Some examples of suitable Hypol® polyurethane prepolymers include Hypol® FHP 2000, Hypol® FHP 2002, and Hypol® FHP 3000. Polyurethane prepolymers other than these Hypol® prepolymers my be used, but not necessarily with equivalent results.

The heterogeneous ion-exchange foam may be prepared and formed into the layer(s) of the reservoir 12 using any suitable procedures. Generally, preparation of the heterogeneous ion-exchange foam involves (i) dispensing and mixing of the ingredients (i.e. prepolymer and ion-exchange substance) of the heterogeneous ion-exchange foam, (ii) blowing, such as by incorporating a blowing agent that is capable of promoting a suitable blowing reaction, such as a creaming reaction, rising reaction, or a full rise reaction, and (iii) gelling, such as via gelling reaction. After preparation, the foam is subjected to a suitable shaping process, such as extrusion, injection molding, compression molding, injection compression molding, or transfer molding, and is subsequently cured to form the layer(s) of the reservoir 12.

During preparation of the heterogeneous ion-exchange foam, the rate of the blowing reaction and the rate of the gelling reaction is determined by catalyst incorporated in the reaction. Examples of the catalyst include tertiary amines, which promote blowing reactions, and organometallics, which promote gelling reactions. Tertiary amines may also help enhance blowing reaction rate, and organometallics may also help enhance gelling reaction rate. Additional blowing beyond that attributable solely to the blowing reaction may be obtained by incorporating an auxiliary blowing agent, such as methylene chloride or a suitable chlorofluorocarbon, such as CFC-11. The use of a silicone-based surfactant will help selectively control cell size and uniformity in the foam by reducing surface tension of the foam ingredients. The silicone-based surfactant may also enhance solubilization of the foam ingredients.

One example of another suitable procedure for forming the heterogeneous ion-exchange foam entails mixing any selected ion-exchange substance(s) with water to form an aqueous suspension. Preferably, the ion-exchange substance (s) is in the form of fine powder to enhance the distribution of the ion-exchange substance in the heterogeneous ion-exchange foam and to enhance the surface area that is available for ion-exchange. The aqueous suspension is combined with the prepolymer component(s) of the foam, such as any of the noted Hypol® prepolymers, with rapid stirring to form a foam mixture. The foam mixture is further agitated until expansion due to foaming subsides. The foam mixture is subjected to a suitable shaping process, such as extrusion, injection molding, compression molding, injection compression molding, or transfer molding, and is subsequently cured to form the layer(s) of the reservoir 12.

The pH buffering reactions occurring in the anode and the cathode of the iontophoresis system, when the reservoir 12 is made of or includes either the ion-exchange copolymer or the heterogeneous ion-exchange foam, may be generally characterized as ion-exchange reactions. pH buffering reactions of any proton sponge included in the reservoir 12 are properly characterized as ion scavenging reactions, and not ion-exchange reactions.

As noted, hydrogen ions ($H^+$) are evolved at the positive electrode (anode) and hydroxide ions ($OH^-$) are evolved at the negative electrode (cathode) by electrolysis of water. Ion-exchange reactions occurring at the anode neutralize hydrogen ions ($H^+$) contained in the electrolytic solution and ionexchange reactions occurring at the cathode neutralize hydroxide ions ($OH^-$) contained in the electrolytic solution.

More particularly, the ion-exchange reaction that occurs in the anode that has the structure of the electrode 10, when the reservoir 12 is formed of or includes the ion-exchange copolymer or the heterogeneous ion-exchange foam, may be characterized according to reaction (1) as follows:

$$—COOK + H^+ \rightarrow —COOH + K^+, \quad (1)$$

where —COOK represents one example of a suitable ion-exchange functionality of either the ion-exchange copolymer or the heterogeneous ion-exchange foam and where —COOH represents the carboxyl group. Additionally, $H^+$ represents hydrogen ion generated by electrolysis of water at the anode, and $K^+$ represents a potassium ion that is released from the ion-exchange functionality by the ionexchange reaction that neutralizes hydrogen ion ($H^+$). Potassium ion ($K^+$) is an example of the adverse ion that is not intended for delivery into the human or animal body. Of course, it is be understood that the ion-exchange functionality incorporated in the electrode 10 may be other than the —COOK functionality and that the ion released from the ion-exchange functionality during the ion-exchange reaction in the anode may be other than $K^+$.

Where the ion-exchange reaction occurs in accordance with reaction (1), it has been found that potassium ions ($K^+$) that are released by the ion-exchange reaction into the electrolytic solution are about five times less mobile than are hydrogen ions ($H^+$). As a result, the undesirable competitive effect between the potassium ion and medicament ions to be delivered to the body is significantly reduced, as compared to the competitive effect between hydrogen ion ($H^+$) and the medicament ions to be delivered to the body. Therefore, the efficiency of medicament ion delivery to the body is considerably improved when the —COOK functionality is incorporated in the reservoir 12 via either the ion-exchange copolymer or the heterogeneous ion-exchange foam. Furthermore, neutralization of the hydrogen ion ($H^+$) makes it possible to maintain the pH at between about 4 and about 8 in the electrolytic solution of the anode that is structured like the electrode 10.

Though the ion-exchange functionality employed at the anode may be other than —COOK and though the adverse ion that is released from the ionexchange functionality may be other potassium ion ($K^+$), the ion-exchange functionality that is selected should release an ion that is at least two times less mobile in the electrolytic solution than hydrogen ion. Preferably, the ionic functionality is selected so that the ion released from the ion-exchange functionality has the same mobility or less mobility in the electrolytic solution than potassium ion.

The ion-exchange reaction that occurs in the cathode that is structured like the electrode 10, when the reservoir 12 is formed of or includes ion-exchange copolymer or heterogeneous ion-exchange foam, actually consists of two separate reaction sequences that may be characterized as reaction (2) and reaction (3) as follows:

$$—COOH + M^+ \rightarrow —COOM + H^+ \quad (2)$$

$$H^+ + OH^- \rightarrow H_2O, \quad (3)$$

In reaction (2), —COOH represents the ion-exchange functionality of the ion-exchange copolymer or the heterogeneous ion-exchange foam included in the reservoir 12 of the electrode 10 that serves as the cathode, and M+ represents metal ion released from the ionic substance by dissociation of the ionic substance in the electrolytic solution of the cathode. As an example, the metal ion released upon dissociation of dexamethasone disodium phosphate, one example of the ionic substance, is sodium ion ($Na^+$). Also, in reaction (2) and reaction (3), $H^+$ represents the hydrogen ion released by the ionic functionality during reaction (2) and $OH^-$ represents the hydroxide ion generated by electrolysis of water at the cathode. Of course, it is to be understood that the ion-exchange functionality incorporated in the ion-exchange copolymer or the heterogeneous ion-exchange foam of the cathode may be other than —COOH and that the ion released upon dissociation of the ionic substance in the cathode may be other than metal ion ($M^+$). The metal ion ($M^+$) depicted in reaction (2) that evolves on dissociation of the ionic substance is another example of the complimentary ion that is not intended for delivery into the human or animal body.

The net result of reaction (2) and reaction (3) is that hydrogen ion ($H^+$) released from the ionic functionality of the cathode reacts with the hydroxide ion ($OH^-$) generated by electrolysis of water at the cathode to produce water ($H_2O$). Since the metal ion ($M^+$) that is dissociated from the ionic species exchanges with the hydrogen ion $H^+$ in reaction (2), the net effect of reaction (2) and reaction (3) is that no adverse or complimentary ion depicted in reaction (2) or reaction (3) remains in the electrolytic solution to compete with the medicament ions for delivery to the body.

In another embodiment of the electrode 10, the permeable material of the reservoir 12 is made of or incorporates any suitable proton sponge. As mentioned, Type A, Type B, and Type C proton sponges are some of the proton sponges of interest. The Type A proton sponge may be prepared by incorporating two or more proton sponge functional groups onto the carrier compound. Each proton sponge functional group consists of a pair of neighboring proton sponge functional group components. The proton sponge functional group components are attached to the carrier compound so that the proton sponge functional group components cooperate together and form the proton sponge functional group.

Tertiary amino groups, such as dialkyl amino groups and di-alkylpyridine groups are examples of suitable proton sponge functional group components for the Type A proton sponge. The diethyl amino group and the dimethyl amino group are examples of suitable dialkyl amino groups, and the di-methylpyridine group and the di-butylpyridine group are examples of suitable di-alkylpyridine groups. Another example of suitable proton sponge functional group components include certain phosphino groups, such as diphenyl phosphino groups.

Assuming for purposes of illustration that the proton sponge functional group components are tertiary amino groups, the tertiary amino groups create strain within the proton sponge which causes the proton sponge to exhibit steric effects. The steric effects cause the proton sponge to be more strongly basic than would be expected from the mere presence of the two tertiary amino groups. Protonation of the proton sponge with hydrogen ion relieves the steric strain and stabilizes the proton sponge. The hydrogen ion resonates between covalent bonding and hydrogen bonding to the nitrogens of the diethyl amino groups such that, at any particular time, the hydrogen ion forms a hydrogen bond with the nitrogen of one of the diethyl amino groups and forms a covalent bond with the nitrogen of the other of the diethyl amino groups.

The carrier compound of the Type A proton sponge may be any organic compound, such as a homocyclic compound, a heterocyclic compound, or a straight or branched organic chain that may, optionally, include hetero atoms in the chain. Additionally, the carrier compound may be any suitable polymer of the homocyclic compound, the heterocyclic compound, or the straight or branched organic chain. To be useful in forming the Type A proton sponge, proton sponge functional group components should be capable of being attached to the carrier compound in neighboring, strained relation to make the proton sponge. The carrier compound may take any physical form, provided that the carrier compound should be insoluble in the solvent of the electrolytic solution and provided that the carrier compound should prevent physical movement, such as diffusion, migration, and electro-migration, of the proton sponge within the electrode 10.

Some examples of organic compounds that are suitable for use as the carrier compound include naphthalene, fluorene, phenanthrene, and isoindene. An example of the Type A proton sponge that includes fluorene as the carrier compound is 4,5bis(dimethylamino)fluorene. An example of the Type A proton sponge that includes phenanthrene as the carrier compound is 4,5-bis(dimethylamino)phenantlrene.

The carrier compound of the Type A proton sponge may also be a copolymer of any two or more different organic compounds. Examples of organic compounds that may be used in forming the copolymer that is useful as the carrier compound include homocyclic compounds, heterocyclic compounds, or straight or branched organic chains that may, optionally, include hetero atoms in the chain. To be suitable for use as the carrier compound, the copolymer should permit attachment of the proton sponge functional group components in neighboring, strained relation to make the proton sponge. Naphthalene/urethane copolymer is an example of the copolymer that may serve as the carrier compound. For the naphthalene/urethane copolymer, suitable proton sponge functional group components, such as diethyl amino groups, may be attached to the naphthalene group in neighboring, strained relation.

As mentioned, the Type B proton sponge may be prepared by incorporating one or more pairs of hetero atoms into the organic core compound at select positions. In the Type B proton sponge, the shape of the organic core compound places the pair of hetero atoms relatively close together and hinders movement of reactants toward the hetero atoms. Protonation of the Type B proton sponge, such as addition of hydrogen ion between adjacent hetero atoms, stabilizes the Type B proton sponge and enables further ionic reaction of the protonated Type B proton sponge. The organic core compound may take any physical form, provided that the organic core compound should be insoluble in the solvent of the electrolytic solution and provided that the organic core compound should prevent physical movement, such as diffusion, migration, and electro-migration, of the proton sponge within the electrode 10.

Some examples of the Type B proton sponge include quino[7,8-h]quinoline, phenanthroline and piperazinyl-naphthyridine. The organic core compound may be any combination of two or more ring compounds, such as pyrol, pyridine, or similar. The organic core compound may be any suitable polymer or copolymer that includes adjacent ring compounds. In the Type B proton sponge, nitrogen is substituted in place of carbon in respective rings of at least two adjacent ring compounds so that adjacent ring nitrogens are spaced in close relation to each other and hinder movement of molecules toward the ring nitrogens of the Type B proton sponge.

As mentioned, the Type C proton sponge may be characterized as the organic support compound that includes at least one hetero atom and at least two attached organic groups. The hetero atom is substituted into the organic support compound in place of carbon. Each of the two organic groups are attached to ring or chain carbons that are next to, and on opposing sides of, the hetero atom. With this structure, the two attached organic groups surround and closely confront the hetero atom.

Benzene-based monomers are some examples of the organic support compound. Other examples of the organic support compound include suitable polymers or copolymers, such as polymers or copolymers that include organic rings, including benzene. The organic support compound may take any physical form, provided that the organic support compound should be insoluble in the solvent of the electrolytic solution and provided that the organic support compound should prevent physical movement, such as diffusion, migration, and electro-migration, of the proton sponge within the electrode 10.

2,6-di-t-butylpyridine is one example of the Type C proton sponge. In the Type C proton sponge that is 2,6-di-t-butylpyridine, pyridine is the organic support compound. Assuming that nitrogen is at the No. 1 position of the ring, 2,6-di-t-butylpyridine may be prepared by attaching tertiary-butyl groups to the No. 2 and the No. 6 positions of the ring, adjacent to, and on either side of the ring nitrogen.

In the Type C proton sponge, the bulky nature of the organic groups that are attached on opposing sides of the hetero atom, such as nitrogen, hinders movement of reactants toward the hetero atom. Protonation of Type C proton sponges, such as addition of hydrogen ion to the hetero atom, such as by covalent bonding, stabilizes the Type C proton sponges and enables further ionic reaction of the protonated Type C proton sponge.

Additional techniques for forming the Type A proton sponge are envisioned. It has been found that proton sponge functional group components, paired in neighboring, strained relation as the proton sponge functional group, may be incorporated into the carrier compound to make the proton sponge in a variety of ways. For example, one or more pairs of proton sponge functional group components may be attached, such as by substitution, in neighboring, strained relation onto a monomeric precursor to make a monomeric sponge group precursor. The monomeric sponge group precursor is then reacted with one or more secondary monomeric precursors to form a proton sponge copolymer that incorporates the proton sponge functional group. The secondary monomeric precursor may generally be any polymerizable compound, such as polymerizable aromatic compounds, polymerizable homocyclic compounds, polymerizable heterocyclic compounds, or polymerizable straight or branched organic chains.

Each monomeric sponge group precursor of the proton sponge copolymer may have the same matched pairs of proton sponge functional group components. Alternatively, there may be two or more different monomeric sponge group precursors that each may include two or more different matched pairs of proton sponge functional group components. Also, one secondary monomeric precursor may be copolymerized with the monomeric sponge group precursor(s) to make the proton sponge copolymer. Alternatively, two or more different secondary monomeric precursors may be copolymerized with the monomeric sponge group precursor(s) to make the proton sponge copolymer. The secondary monomeric precursor(s) may be copolymerized with the monomeric sponge group precursor(s) to form the proton sponge copolymer using any conventional copolymerization technique that is suitable for polymerizing precursors included in the proton sponge copolymer.

A polymerizable monomer, such as a polymerizable naphthalene-based monomer, that includes a pair of substituted proton sponge group components is one example of the monomeric sponge group precursor of the proton sponge copolymer. Though some monomers, such as a naphthalene-based compound that includes only a single naphthalene group per molecule, may accommodate only a single pair of proton sponge group components, other polymerizable monomers that may include two or more pairs of proton sponge group components may be used as the monomeric sponge group precursor of the proton sponge copolymer. Additional examples of monomers that may be suitably combined with proton sponge functional group components to make the monomeric sponge group precursor include polymerizable fluorene-based compounds, polymerizable phenanthrene-based compounds, polymerizable isoindene-based compounds, and any other polymerizable compound that is capable of forming a structural network that imposes a close proximity, strained formation on neighboring pairs of proton sponge functional group components.

Other possibilities for forming the Type A proton sponge exist. For example, matched pairs of proton sponge functional group components, or any monomeric sponge group precursor, may be chemically attached to the carrier compound to make a substituted proton sponge polymer or copolymer.

Examples of the carrier compound suitable for making the substituted proton sponge polymer include various polymers, such as homopolymers based on naphthalene; fluorene; phenanthrene; isoindene; various urethanes, such as etheric and esteric urethanes; vinyl alcohol; vinyl pyrolidone; acryl amide; carbohydrate; ethylene oxide; and hydroxyalkylmethacrylate. Examples of the carrier compound suitable for making the substituted proton sponge copolymer include various copolymers, such as copolymers based on any two or more of the following: naphthalene; fluorene; phenanthrene; isoindene; various urethanes, such as etheric and esteric urethanes; vinyl alcohol; vinyl pyrolidone; acryl amide; carbohydrate; ethylene oxide; and hydroxyalkylmethacrylate. As an example, naphthalene/urethane copolymer may be used as the carrier compound of the substituted proton sponge copolymer. Examples of functional groups for the urethane that may be used in making the substituted proton sponge polymer or copolymer include (1) diol groups and diisocyanate groups and (2) triol groups and tri-isocyanate groups.

Examples of proton sponge functional group components suitable for chemical attachment onto the carrier compound to make the substituted proton sponge polymer or the substituted proton sponge copolymer include tertiary amino groups, such as dialkyl amino groups and di-alkylpyridine groups. The diethyl amino group and the dimethyl amino group are examples of suitable dialkyl groups, and the di-methylpyridine group and the di-butylpyridine group are examples of suitable di-alkylpyridine groups.

The proton sponge of the present invention may also be heterogeneously incorporated in suitable foam to make a heterogeneous proton sponge foam. Heterogeneous proton sponge foam is made by dispersing the proton sponge in one or more prepolymer components of polymer or copolymer foam, prior to reacting the prepolymer components to make the polymer or copolymer foam. In the heterogeneous proton sponge foam, the proton sponge is physically entrapped within the structure of the polymer or copolymer foam. The molecular weight of the proton sponge that is incorporated in the polymer or copolymer foam should be at least about 5000 daltons (grams per mole) to immobilize the proton sponge in the polymer or copolymer foam. Preferably, the polymer or copolymer foam portion of the heterogeneous proton sponge foam is an open cell foam that supports enhanced movement of the electrolytic solution within the heterogeneous proton sponge foam.

After formation of the heterogeneous proton sponge foam, the polymer or copolymer foam and the proton sponge form distinct phases of the heterogeneous proton sponge foam. Heterogeneous proton sponge foam includes at least two distinct phases. For any electrode that includes the heterogeneous proton sponge foam, each of the phases should be insoluble in the solvent portion of any electrolytic solution included in the electrode to immobilize physical movement of any component of the heterogeneous proton sponge foam within the electrode. The phases may each be solid or semi-solid in nature. Alternatively, some phase(s) may be solid in nature, and other phase(s) may be semi-solid in nature. The proton sponge makes one or more of the phases, and polymer foam or copolymer foam makes up the other phase(s).

Other examples of heterogeneous proton sponge materials include various composite polymer mixtures of host polymeric material and proton sponge. The host polymeric material may be formed as a gel, a membrane, a hydrocolloid, fibers, a laminate, particles, granules, or other suitable matrix. The proton sponge may be dispersed within the host polymeric material, such as by impregnating the proton sponge within the host polymeric material either before or after formation of the host polymeric material. The molecular weight of the proton sponge that is incorporated in the host polymeric material should be at least about 5000 daltons (grams per mole) to immobilize and physically entrap the proton sponge within the host polymeric material. The proton sponge may also be coated onto the host polymeric material. When the host polymer material is a loose material, such as in the form of particles or granules, the reservoir 12 may include suitable boundary layers (not shown) for containing the host material within the reservoir 12.

The heterogeneous proton sponge foam may be prepared and formed into the layer(s) of the reservoir 12 using any suitable procedure. For example the heterogeneous proton sponge foam may be prepared and formed using the procedures already described for preparing and forming the heterogeneous ion-exchange foam, with the exception that the proton sponge is substituted in place of the ion-exchange substance in the process steps. Any proton sponge, such as the Type A proton sponge, the Type B proton sponge, and the Type C proton sponge, may be incorporated in the heterogeneous proton sponge foam. Examples of prepolymer that are suitable for use in forming the heterogeneous proton sponge foam include each of the prepolymers described for use in preparing the heterogeneous ion-exchange foam.

Alternatively, homogeneous proton sponge foam may be prepared by introducing any type or form of the proton sponge, in any combination, onto previously prepared homogeneous foam by suitable surface or penetrating treatment, provided that the molecular weight of the proton sponge that is used to make the homogeneous proton sponge foam should have a molecular weight of at least about 5000 daltons (grams per mole) to immobilize the proton sponge within the homogeneous proton sponge foam.

Illustrative examples of proton sponges that may be incorporated in the homogeneous proton sponge foam include any suitable Type A, Type B or Type C proton sponges, or a mixture of any of these types of proton sponges. Some particular examples of the proton sponge that be may introduced onto the homogeneous foam to make the homogeneous proton sponge foam include 1,8-Bis(diethylamino)-2,7-dimethoxynaphthalene, 4,5bis(dimethylamino)fluorene, 4,5bis(dimethylamino)phenanthrene, quino[7,8-h] quinoline, phenanthroline, piperazinyl-naphthyridine, 2,6-di-t-butylpyridine, derivatives of these, and analogues of these.

Suitable homogeneous foams for use in preparing the homogeneous proton sponge foam include phenol-formaldehyde, polyurethane, polyethylene, and polyvinyl alcohol. The precursor components of the homogeneous proton sponge foam may be reacted to form the homogeneous proton sponge foam using any conventional foam formation process that is suitable for the particular precursor components selected.

It should also be understood that, either before, during, or after formation of the permeable material, the proton sponge may be dispersed within any permeable material in addition to heterogeneous or homogeneous foam to incorporate the proton sponge in the reservoir 12. Also, either before, during, or after formation of the permeable material, proton sponge functional groups or compounds that include proton sponge functional groups, may be dispersed within any permeable material, including heterogeneous and homogeneous foam, to incorporate the proton sponge functional groups in the reservoir 12 as the proton sponge. The molecular weight of any proton sponge or proton sponge functional groups that are dispersed in the permeable material should be at least about 5000 daltons (grams per mole) to immobilize the proton sponge or proton sponge functional groups within the permeable material.

Other techniques for incorporating the proton sponge into the electrode 10, in addition to dispersing the proton sponge within the permeable material, are envisioned. For example, the proton sponge may be placed separate from the reservoir 12, within the electrode 10 depicted in FIG. 1 or the electrode 110 depicted in FIG. 2, as a proton sponge layer (not shown) between the conductive layer 14 and the reservoir 12 and adjacent to the reservoir 12. In this version of the electrode 10 or the electrode 110, the permeable material used to form the reservoir 12 may be any conductive material that is capable of accepting the electrolytic solution. As another example, the proton sponge may be placed within the electrode 210 depicted in FIG. 3, separate from the reservoir 212, as a proton sponge layer (not shown) that is located between and the reservoir 212 and the adhesive layer 20. In this version of the electrode 210, the permeable material used to form the reservoir 212 may be any conductive material that is capable of accepting the electrolytic solution.

One example of the Type A proton sponge is the copolymer which has the structure provided in graphic formula V:

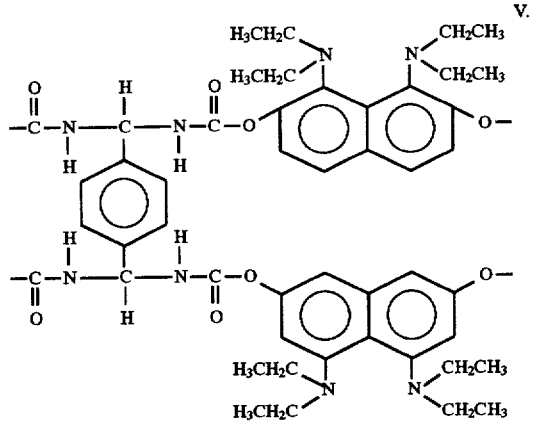

V.

The copolymer of formula V is from about 20% to about 30% 1,8-di-(diethylamino)-naphthalene, by weight, and from about 70% to about 80% urethane, by weight. The copolymer of formula V may be formed by substituting the diethyl amino groups onto the naphthalene group to form a substituted naphthalene-based compound before copolymerizing the substituted naphthalene-based compound and the urethane compound. The substituted naphthalene-based compound and the urethane compound may be copolymerized using any conventional copolymerization process that preserves the structural integrity of the substituted naphthalene-based compound. Alternatively, the diethyl amino groups may be substituted onto the naphthalene group after copolymerizing the naphthalene-based compound and the urethane compound. The naphthalene-based compound and the urethane compound may be copolymerized using any conventional copolymerization process.

After scavenging hydrogen ion (H$^+$) at the anode, the proton sponge of graphic formula V has the protonated structure of graphic VI and is able to bond with anions, such as chloride ion released on dissociation of lidocaine hydrochloride:

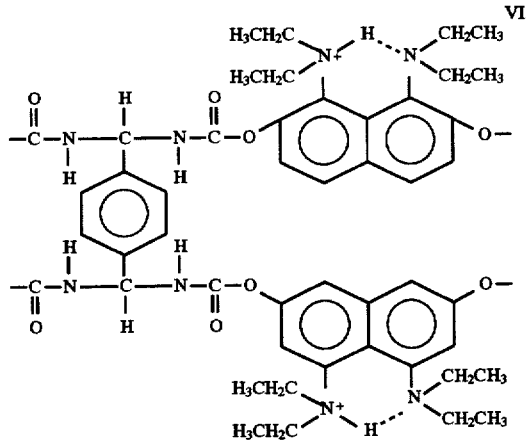

VI.

In the protonated proton sponge of graphic formula VI, the hydrogen ion resonates between covalent bonding and hydrogen bonding to one of the diethyl amino groups and resonates between hydrogen bonding and covalent bonding with the other of the diethyl amino groups. Thus, at any particular time, the hydrogen ion forms a hydrogen bond with the nitrogen of one of the diethyl amino groups and forms a covalent bond with the nitrogen of the other of the diethyl amino groups. After bonding with the chloride ion that is released on dissociation of lidocaine hydrochloride, the protonated proton sponge of graphic formula VI has the structure of graphic formula VII:

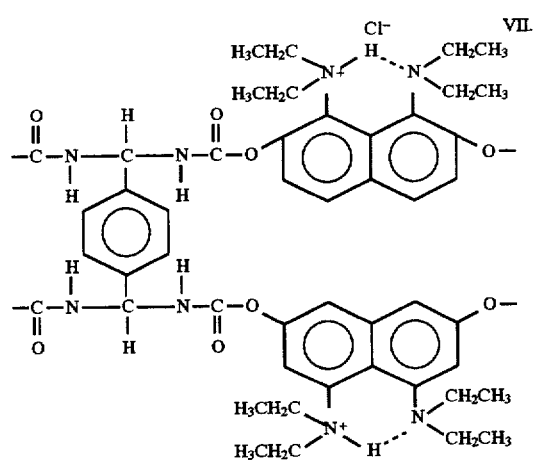

VII.

Though the chloride ion has bonded with the protonated proton sponge, no adverse ions were released by the protonated proton sponge to compete with medicament ions for delivery to the body.

Another example of the Type A proton sponge is 1,8bis(diethylamino) naphthalene, which has the structure of graphic formula VIII:

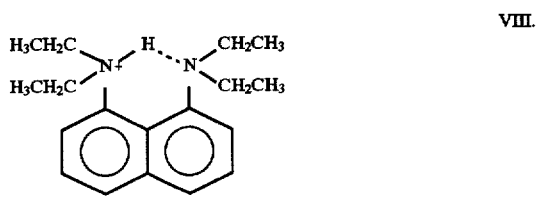

VIII.

The proton sponge of graphic formula VIII includes naphthalene as the carrier compound and diethyl amino groups as the matched proton sponge functional component groups. The proton sponge of graphic formula VIII may be incorporated into the iontophoresis system in a number of ways. For example, the proton sponge of graphic formula VIII may be covalently attached to a suitable polymer or copolymer chain that is subsequently dispersed within the permeable material that forms the reservoir 12.

No matter how the proton sponge is incorporated in the electrode 10, the electrode 110, or the electrode 210, the proton sponge functional group, when employed in the anode of the iontophoresis system, effectively scavenges hydrogen ions (H$^+$) generated at the anode by electrolysis of water via a protonation reaction. Using the Type A proton sponge of graphic formula VIII for purposes of illustrating the reaction, the protonation reaction may be represented by reaction (4):

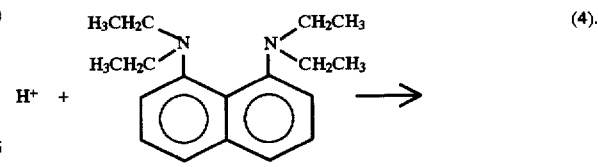

(4).

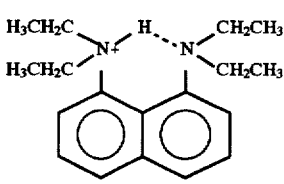

In reaction (4), the Type A proton sponge scavenges hydrogen ion (H⁺) released during electrolysis of water at the anode. The hydrogen ion (H⁺) resonates between covalent bonding (represented by the solid line) and hydrogen bonding to the nitrogen of one of the proton sponge functional group components and resonates between hydrogen bonding (represented by the dashed line) and covalent bonding to the nitrogen of the other of the proton sponge functional group components. Thus, at any particular time, the hydrogen ion forms a hydrogen bond with the nitrogen of one of the proton sponge group components and forms a covalent bond with the nitrogen of the other of the proton sponge functional group components.

Though the proton sponge functional group components in reaction (4) are depicted as diethyl amino groups, it is to be understood that the proton sponge functional group components involved in reaction (4) may be any suitable proton sponge functional group components, including diethyl amino groups. Also, though the carrier compound in reaction (4) is depicted as naphthalene, it is to be understood that the carrier compound involved in reaction (4) may be any suitable carrier compound.

The second step of the proton sponge reaction sequence is represented by reaction (5):

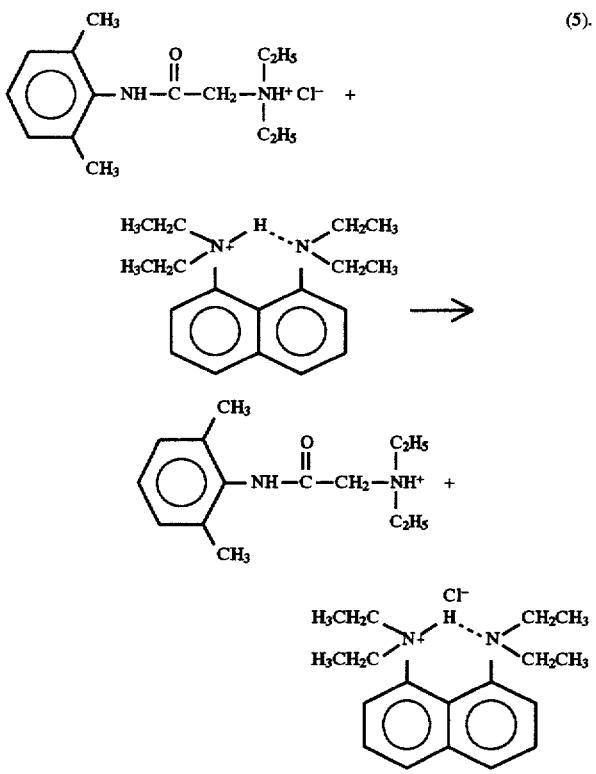

In reaction (5), the anion, chloride (Cl⁻), combines with the protonated proton sponge to counterbalance the positively charged protonated proton sponge. The chloride ion (Cl⁻) enters the electrolytic solution when the lidocaine hydrochloride dissociates in the electrolytic solution. It should be understood that reaction of the protonated proton sponge, as in reaction (5), will vary in extent, depending upon the ionic substance employed at the anode, since some complimentary anions of medicament cations may form insoluble salts with any counter ions present in the electrolytic solution, rather than bonding with the protonated proton sponge.

The proton sponge functional group may be incorporated in either the anode or the cathode of the iontophoresis system. However, the proton sponge functional group is most beneficial when incorporated into the anode structured like the electrode 10, since hydrogen ions (H⁺) are not typically generated at the cathode and since the proton sponge is incapable of scavenging hydroxide ion (OH⁻).

Though the proton sponge functional group in reaction (5) is depicted as a pair of diethyl amino groups, it is to be understood that the proton sponge functional group involved in reaction (5) may be any suitable proton sponge functional group, including a pair of diethyl amino groups. Also, though the carrier compound in reaction (5) is depicted as naphthalene, it is to be understood that the carrier compound involved in reaction (5) may be any suitable carrier compound. Furthermore, though the ionic species in reaction (5) is depicted as lidocaine hydrochloride, it is to be understood that the ionic species involved in reaction (5) may be any suitable ionic species, including lidocaine hydrochloride, that frees an anion for bonding with the protonated proton functional sponge.

For the electrode 10 that includes lidocaine hydrochloride as the ionic species in the reservoir 12, the proton sponge functional group that is selected should have a dissociation constant, $pK_a$, that is approximately equal to the $pK_a$ of lidocaine hydrochloride of approximately 8 to minimize, and preferably prevent, conversion of the lidocaine hydrochloride into lidocaine base and to promote protonation of the proton sponge functional group. If the $pK_a$ value of the proton sponge functional group is higher than the $pK_a$ value of lidocaine hydrochloride, the proton sponge functional group tends to attract hydrogen ion (H⁺) from the lidocaine hydrochloride, thus converting lidocaine hydrochloride into the less beneficial lidocaine base. On the other hand, if the $pK_a$ value of the proton sponge functional group is somewhat less than the $pK_a$ value of lidocaine hydrochloride, protonation of the proton sponge functional group with hydrogen ion (H⁺) arising from electrolysis of water at the anode tends to decrease in extent.

No matter how the proton sponge functional group is incorporated in the anode of the iontophoresis system, the electrode 10 that includes the proton sponge functional group exhibits superior qualities, even as compared to the electrode 10 that includes the ion-exchange copolymer or the heterogeneous ion-exchange foam. Specifically, the proton sponge functional group, like the ion-exchange copolymer and the heterogeneous ion-exchange foam, remedies the pH shift problem found in prior art electrodes by binding hydrogen ions (H⁺) generated by electrolysis of water. Additionally, unlike the ion-exchange copolymer and the heterogeneous ion-exchange foam, the proton sponge functional group does not release any ions that will compete with medicament ions for delivery to the body. This effect is observed because the proton sponge functional group traps the hydrogen ion (H⁺) via a scavenging reaction, rather than via ion-exchange.

The electrode of the present invention represents a milestone in the development of advanced iontophoresis systems. In addition to the benefits of proton sponge incorporation into the inventive electrode, other important benefits exist. For example, one significant benefit of the electrode 10 is the ability to closely and accurately control the dosage of any pH buffering material that is included in the reservoir 12. Incorporation of the pH buffering material into the reservoir 12 secures the pH buffering material within the structure of the reservoir 12 and prevents losses of pH buffering material from the reservoir 12 during assembly, handling, and use of the electrode. Another significant benefit of the electrode 10 is the ability to closely and accurately control the dosage of any proton sponge functional groups that are included in the reservoir 12. Incorporation of the proton sponge into the reservoir 12 secures the proton sponge functional groups within the structure of the reservoir 12 and prevents losses of proton sponge functional groups from the reservoir 12 during assembly, handling, and use of the electrode.

In practice, use of the iontophoresis system that includes the cathode and/or the anode, that is structured like the electrode 10, is efficient and convenient. Where the active electrode of the iontophoresis system is structured like the electrode 10, the electrolytic solution may be injected into the reservoir 12 of the electrode 10 after formation of the electrode 10 using any conventional technique, such as with a hypodermic syringe. Medicament ions that will be delivered to the body are typically included in the electrolytic solution by dissociating the ionic substance of interest in the appropriate solvent before the electrolytic solution is injected into the reservoir 12. For electrodes that will not be used to iontophoretically deliver medicament ions, the electrolytic solution that includes the conductive ions may be injected into the reservoir 12 of the electrode 10 after formation of the electrode 10 using any conventional technique, such as with the hypodermic syringe. Furthermore, as already explained, different medicament ions may be placed in the different electrolytic solutions that are placed in the cathode and the anode, for simultaneous iontophoretic delivery from both the cathode and the anode.

Next, both of the electrodes of the iontophoresis system are attached to the surface of the body, such as the skin of the patient. For any electrode of the iontophoresis system that is structured like the electrode 10, the reservoir 12 faces the skin, the terminal 16 faces away from the skin, and the adhesive cover 20 is attached to the skin to secure the electrode 10 to the body. If the ground electrode of the iontophoresis system is structured like the electrode 10, the terminal 16 of the electrode 10 is comiected to the source of electrical power to support current flow through the body. If the active electrode of the iontophoresis system is structured like the electrode 10, the terminal 16 of the electrode 10 is connected to the source of electrical power to initiate delivery of medicament ions into the body.

It should also be understood that the anode and the cathode may also be connected to the source of electrical power such that the iontophoresis electrode that includes the anode structured like the electrode 10 and/or the cathode structured like the electrode 10 is capable of providing suitable current flow to the body to stimulate a muscle of the body. In this application, the electrode 10 may include either electrolytic solution that includes medicament ions, if delivery of medicament ions will coincide with muscle stimulation. Alternatively, the electrode 10 may include electrolytic solution that is free of medicament ions and that includes conductive ions, if delivery of medicament ions will not coincide with muscle stimulation. In the case of muscle stimulation alone, the current source would supply an appropriate current form, such as alternating current.

Although the present invention has been described with reference to preferred embodiments, workers skilled in the art will recognize that changes may be made in form and detail without departing from the spirit and scope of the invention.

What is claimed is:

1. A pH buffered electrode comprising:

a reservoir for holding electrolytic solution, the reservoir comprising foam;

a pH buffer, the pH buffer chemically bonded to the foam; and;

an electrical connection in electrical communication with the reservoir.

2. The pH buffered electrode of claim 1 wherein the foam is selected from the group consisting of phenol-formaldehyde; polyurethane; polyethylene; polyvinyl alcohol; any copolymer of phenol-formaldehyde, polyurethane, polyethylene, and polyvinyl alcohol; and a mixture of any of these.

3. The pH buffered electrode of claim 1 wherein the pH buffer comprises ion exchange material.

4. The pH buffered electrode of claim 1 wherein the pH buffer comprises a proton sponge or a functional group capable of scavenging ions.

5. The pH buffered electrode of claim 1, and further comprising carbonized particles, the carbonized particles dispersed within and immobilized within the reservoir, the carbonized particles capable of making the reservoir conductive.

6. The pH buffered electrode of claim 1, the electrode further comprising electrolytic solution, the reservoir holding all, or substantially all, of the electrolytic solution that is comained in the electrode.

7. A use of the pH buffered electrode of claim 1, the use comprising:

injecting electrolytic solution into the reservoir;

locating the electrode against a surface of a body with the reservoir in working relation with the surface of the body; and connecting the electrial connection to a source of electrical power.

8. A method of making a pH buffered electrode, the method comprising:

chemically bonding a pH buffer to a foam;

creating a reservoir for holding electrolytic solution, the reservoir comprising the pH buffer and the foam; and placing an electrical connection in electrical communication with the reservoir.

9. The method of claim 8 wherein the foam is selected from the group consisting of phenol-formaldehyde; polyurethane; polyethylene; polyvinyl alcohol; any copolymer of phenol-formaldehyde, polyurethane, polyethylene, and polyvinyl alcohol; and a mixture of any of these.

10. The method of claim 8 wherein the pH buffer comprises ion exchange material.

11. The method of claim 8 wherein the pH buffer comprises a proton sponge or a functional group capable of scavenging ions.

12. The method of claim 8, the method further comprising dispersing and immobilizing carbonized particles within the reservoir, the carbonized particles capable of making the reservoir conductive.

13. The method of claim 8, the method further comprising filling the reservoir with electrolytic solution, the reservoir holding all, or substantially all, of the electrolytic solution that is contained in the electrode.

14. A pH buffered electrode made by the method of claim 8.

15. The use of a pH buffered electrode made by the method of claim 8, the use comprising:

injecting electrolytic solution into the reservoir;

locating the electrode against a surface of a body with the reservoir in working relation with the surface of the body; and connecting the electrical connection to a source of electrical power.

* * * * *

UNITED STATES PATENT AND TRADEMARK OFFICE
CERTIFICATE OF CORRECTION

PATENT NO. : 5,788,666
DATED : AUGUST 4, 1998
INVENTOR(S) : LJILJANA ATANASOSKA

It is certified that error appears in the above-identified patent and that said Letters Patent is hereby corrected as shown below:

Col. 2, line 33, delete "fuither", insert --further--

Col. 10, line 7, delete "finctionality", insert --functionality--

Col. 10, line 8, delete "WVhen", insert --When--

Col. 13, line 58, after "electrode", insert --10--

Col. 14, line 4, delete "10 olms", insert --10 ohms--

Col. 14, line 6, after "electrode", insert --10--

Col. 14, lines 64-65, delete "VERA-TEC", insert --VERSA-TEC--

Col. 24, line 21, delete "phenanthrene", insert --phenanthene--.

Col. 33, line 48, delete "comiected", insert --connected--

Signed and Sealed this

Eighteenth Day of April, 2000

Attest:

Q. TODD DICKINSON

*Attesting Officer*     *Director of Patents and Trademarks*

UNITED STATES PATENT AND TRADEMARK OFFICE
CERTIFICATE OF CORRECTION

PATENT NO : 5,788,666

DATED : August 4, 1998

INVENTOR(S) : Ljiljana Atanasoska

It is certified that error appears in the above-identified patent and that said Letters Patent are hereby corrected as shown below:

Col. 24, line 21, delete "phenanthene", insert --phenanthrene--.

Col. 24, line 22, delete "4,5-bis(dimethylamino)phenantlrene", insert --4,5-bis(dimethylamino)phenanthrene--.

Signed and Sealed this

Third Day of April, 2001

Attest:

NICHOLAS P. GODICI

Attesting Officer

Acting Director of the United States Patent and Trademark Office